US012805937B2

(12) United States Patent
Paul et al.

(10) Patent No.: US 12,805,937 B2
(45) Date of Patent: Nov. 24, 2026

(54) COMPUTER ASSISTED SURGERY NAVIGATION MULTI-POSTURE IMAGING BASED KINEMATIC SPINE MODEL

(71) Applicant: GLOBUS MEDICAL, INC., Audubon, PA (US)

(72) Inventors: David C. Paul, Phoenixville, PA (US); George Yacoub, Lansdale, PA (US); Shubo Wang, Malvern, PA (US)

(73) Assignee: Globus Medical Inc., Audubon, PA (US)

( * ) Notice: Subject to any disclaimer, the term of this patent is extended or adjusted under 35 U.S.C. 154(b) by 321 days.

(21) Appl. No.: 18/437,418

(22) Filed: Feb. 9, 2024

(65) Prior Publication Data

US 2025/0255670 A1 Aug. 14, 2025

(51) Int. Cl.

| | |
|---|---|
| ***A61B 34/10*** | (2016.01) |
| ***A61B 5/107*** | (2006.01) |
| ***A61B 17/70*** | (2006.01) |
| ***A61B 17/86*** | (2006.01) |
| ***A61B 34/20*** | (2016.01) |
| ***A61B 34/30*** | (2016.01) |
| ***G06T 7/00*** | (2017.01) |
| ***G16H 20/40*** | (2018.01) |
| ***G16H 50/50*** | (2018.01) |

(52) U.S. Cl.

CPC ............ *A61B 34/10* (2016.02); *A61B 5/1079* (2013.01); *A61B 17/70* (2013.01); *A61B 17/86* (2013.01); *A61B 34/20* (2016.02); *A61B 34/30* (2016.02); *G06T 7/0016* (2013.01); *G16H 20/40* (2018.01); *G16H 50/50* (2018.01); *A61B 2034/105* (2016.02); *A61B 2034/2065* (2016.02); *G06T 2207/30012* (2013.01)

(58) Field of Classification Search

CPC ....... A61B 34/10; A61B 5/1079; A61B 17/70; A61B 17/86; A61B 34/20; A61B 34/30; A61B 2034/105; A61B 2034/2065; A61B 2034/104; A61B 2034/2055; G06T 7/0016; G06T 2207/30012; G16H 20/40; G16H 50/50

See application file for complete search history.

(56) References Cited

U.S. PATENT DOCUMENTS

| | | | |
|---|---|---|---|
| 4,150,293 | A | 4/1979 | Franke |
| 5,246,010 | A | 9/1993 | Gazzara et al. |
| 5,354,314 | A | 10/1994 | Hardy et al. |
| 5,397,323 | A | 3/1995 | Taylor et al. |
| 5,598,453 | A | 1/1997 | Baba et al. |

(Continued)

OTHER PUBLICATIONS

US 8,231,638 B2, 07/2012, Swarup et al. (withdrawn)

*Primary Examiner* — Richard G Louis

(57) ABSTRACT

A surgical planning system is disclosed which provides computer assisted navigation for spinal surgery. The surgical planning system includes a computer platform operative to obtain images of at least two different postures of a patient's spine, and to measure displacement of anatomical features of the patient's spine between the images of the at least two different postures of the patient's spine. The computer platform is further operative to estimate stiffness of the patient's spine based on the measurements of displacement, and to generate a patient-specific kinematic model of the patient's spine based on the estimated stiffness, and provides a surgical plan based on the patient-specific kinematic model of the patient's spine.

20 Claims, 9 Drawing Sheets

(56) References Cited

U.S. PATENT DOCUMENTS 5,772,594 A 6/1998 Barrick
5,791,908 A 8/1998 Gillio
5,820,559 A 10/1998 Ng et al.
5,825,982 A 10/1998 Wright et al.
5,887,121 A 3/1999 Funda et al.
5,911,449 A 6/1999 Daniele et al.
5,951,475 A 9/1999 Gueziec et al.
5,987,960 A 11/1999 Messner et al.
6,012,216 A 1/2000 Esteves et al.
6,031,888 A 2/2000 Ivan et al.
6,033,415 A 3/2000 Mittelstadt et al.
6,080,181 A 6/2000 Jensen et al.
6,106,511 A 8/2000 Jensen
6,122,541 A 9/2000 Cosman et al.
6,144,875 A 11/2000 Schweikard et al.
6,157,853 A 12/2000 Blume et al.
6,167,145 A 12/2000 Foley et al.
6,167,292 A 12/2000 Badano et al.
6,201,984 B1 3/2001 Funda et al.
6,203,196 B1 3/2001 Meyer et al.
6,205,411 B1 3/2001 DiGioia, III et al.
6,212,419 B1 4/2001 Blume et al.
6,231,565 B1 5/2001 Tovey et al.
6,236,875 B1 5/2001 Bucholz et al.
6,246,900 B1 6/2001 Cosman et al.
6,301,495 B1 10/2001 Gueziec et al.
6,306,126 B1 10/2001 Montezuma
6,312,435 B1 11/2001 Wallace et al.
6,314,311 B1 11/2001 Williams et al.
6,320,929 B1 11/2001 Von Der Haar
6,322,567 B1 11/2001 Mittelstadt et al.
6,325,808 B1 12/2001 Bernard et al.
6,340,363 B1 1/2002 Bolger et al.
6,377,011 B1 4/2002 Ben-Ur
6,379,302 B1 4/2002 Kessman et al.
6,402,762 B2 6/2002 Hunter et al.
6,424,885 B1 7/2002 Niemeyer et al.
6,447,503 B1 9/2002 Wynne et al.
6,451,027 B1 9/2002 Cooper et al.
6,477,400 B1 11/2002 Barrick
6,484,049 B1 11/2002 Seeley et al.
6,487,267 B1 11/2002 Wolter
6,490,467 B1 12/2002 Bucholz et al.
6,490,475 B1 12/2002 Seeley et al.
6,499,488 B1 12/2002 Hunter et al.
6,501,981 B1 12/2002 Schweikard et al.
6,507,751 B2 1/2003 Blume et al.
6,535,756 B1 3/2003 Simon et al.
6,560,354 B1 5/2003 Maurer, Jr. et al.
6,565,554 B1 5/2003 Niemeyer
6,587,750 B2 7/2003 Gerbi et al.
6,614,453 B1 9/2003 Suri et al.
6,614,871 B1 9/2003 Kobiki et al.
6,619,840 B2 9/2003 Rasche et al.
6,636,757 B1 10/2003 Jascob et al.
6,645,196 B1 11/2003 Nixon et al.
6,666,579 B2 12/2003 Jensen
6,669,635 B2 12/2003 Kessman et al.
6,701,173 B2 3/2004 Nowinski et al.
6,757,068 B2 6/2004 Foxlin
6,782,287 B2 8/2004 Grzeszczuk et al.
6,783,524 B2 8/2004 Anderson et al.
6,786,896 B1 9/2004 Madhani et al.
6,788,018 B1 9/2004 Blumenkranz
6,804,581 B2 10/2004 Wang et al.
6,823,207 B1 11/2004 Jensen et al.
6,827,351 B2 12/2004 Graziani et al.
6,837,892 B2 1/2005 Shoham
6,839,612 B2 1/2005 Sanchez et al.
6,856,826 B2 2/2005 Seeley et al.
6,856,827 B2 2/2005 Seeley et al.
6,879,880 B2 4/2005 Nowlin et al.
6,892,090 B2 5/2005 Verard et al.
6,920,347 B2 7/2005 Simon et al.
6,922,632 B2 7/2005 Foxlin
6,968,224 B2 11/2005 Kessman et al.
6,978,166 B2 12/2005 Foley et al.
6,988,009 B2 1/2006 Grimm et al.
6,991,627 B2 1/2006 Madhani et al.
6,996,487 B2 2/2006 Jutras et al.
6,999,852 B2 2/2006 Green
7,007,699 B2 3/2006 Martinelli et al.
7,016,457 B1 3/2006 Senzig et al.
7,043,961 B2 5/2006 Pandey et al.
7,062,006 B1 6/2006 Pelc et al.
7,063,705 B2 6/2006 Young et al.
7,072,707 B2 7/2006 Galloway, Jr. et al.
7,083,615 B2 8/2006 Peterson et al.
7,097,640 B2 8/2006 Wang et al.
7,099,428 B2 8/2006 Clinthorne et al.
7,108,421 B2 9/2006 Gregerson et al.
7,130,676 B2 10/2006 Barrick
7,139,418 B2 11/2006 Abovitz et al.
7,139,601 B2 11/2006 Bucholz et al.
7,155,316 B2 12/2006 Sutherland et al.
7,164,968 B2 1/2007 Treat et al.
7,167,738 B2 1/2007 Schweikard et al.
7,169,141 B2 1/2007 Brock et al.
7,172,627 B2 2/2007 Fiere et al.
7,194,120 B2 3/2007 Wicker et al.
7,197,107 B2 3/2007 Arai et al.
7,231,014 B2 6/2007 Levy
7,231,063 B2 6/2007 Naimark et al.
7,239,940 B2 7/2007 Wang et al.
7,248,914 B2 7/2007 Hastings et al.
7,301,648 B2 11/2007 Foxlin
7,302,288 B1 11/2007 Schellenberg
7,313,430 B2 12/2007 Urquhart et al.
7,318,805 B2 1/2008 Schweikard et al.
7,318,827 B2 1/2008 Leitner et al.
7,319,897 B2 1/2008 Leitner et al.
7,324,623 B2 1/2008 Heuscher et al.
7,327,865 B2 2/2008 Fu et al.
7,331,967 B2 2/2008 Lee et al.
7,333,642 B2 2/2008 Green
7,339,341 B2 3/2008 Oleynikov et al.
7,366,562 B2 4/2008 Dukesherer et al.
7,379,790 B2 5/2008 Toth et al.
7,386,365 B2 6/2008 Nixon
7,422,592 B2 9/2008 Morley et al.
7,435,216 B2 10/2008 Kwon et al.
7,440,793 B2 10/2008 Chauhan et al.
7,460,637 B2 12/2008 Clinthorne et al.
7,466,303 B2 12/2008 Yi et al.
7,493,153 B2 2/2009 Ahmed et al.
7,505,617 B2 3/2009 Fu et al.
7,533,892 B2 5/2009 Schena et al.
7,542,791 B2 6/2009 Mire et al.
7,555,331 B2 6/2009 Viswanathan
7,567,834 B2 7/2009 Clayton et al.
7,594,912 B2 9/2009 Cooper et al.
7,606,613 B2 10/2009 Simon et al.
7,607,440 B2 10/2009 Coste-Maniere et al.
7,623,902 B2 11/2009 Pacheco
7,630,752 B2 12/2009 Viswanathan
7,630,753 B2 12/2009 Simon et al.
7,643,862 B2 1/2010 Schoenefeld
7,660,623 B2 2/2010 Hunter et al.
7,661,881 B2 2/2010 Gregerson et al.
7,683,331 B2 3/2010 Chang
7,683,332 B2 3/2010 Chang
7,689,320 B2 3/2010 Prisco et al.
7,691,098 B2 4/2010 Wallace et al.
7,702,379 B2 4/2010 Avinash et al.
7,702,477 B2 4/2010 Tuemmler et al.
7,711,083 B2 5/2010 Heigl et al.
7,711,406 B2 5/2010 Kuhn et al.
7,720,523 B2 5/2010 Omernick et al.
7,725,253 B2 5/2010 Foxlin
7,726,171 B2 6/2010 Langlotz et al.
7,742,801 B2 6/2010 Neubauer et al.
7,751,865 B2 7/2010 Jascob et al.
7,760,849 B2 7/2010 Zhang
7,762,825 B2 7/2010 Burbank et al.

(56) References Cited

U.S. PATENT DOCUMENTS 7,763,015 B2 7/2010 Cooper et al.
7,787,699 B2 8/2010 Mahesh et al.
7,796,728 B2 9/2010 Bergfjord
7,813,838 B2 10/2010 Sommer
7,818,044 B2 10/2010 Dukesherer et al.
7,819,859 B2 10/2010 Prisco et al.
7,824,401 B2 11/2010 Manzo et al.
7,831,294 B2 11/2010 Viswanathan
7,834,484 B2 11/2010 Sartor
7,835,557 B2 11/2010 Kendrick et al.
7,835,778 B2 11/2010 Foley et al.
7,835,784 B2 11/2010 Mire et al.
7,840,253 B2 11/2010 Tremblay et al.
7,840,256 B2 11/2010 Lakin et al.
7,843,158 B2 11/2010 Prisco
7,844,320 B2 11/2010 Shahidi
7,853,305 B2 12/2010 Simon et al.
7,853,313 B2 12/2010 Thompson
7,865,269 B2 1/2011 Prisco et al.
D631,966 S 2/2011 Perloff et al.
7,879,045 B2 2/2011 Gielen et al.
7,881,767 B2 2/2011 Strommer et al.
7,881,770 B2 2/2011 Melkent et al.
7,886,743 B2 2/2011 Cooper et al.
RE42,194 E 3/2011 Foley et al.
RE42,226 E 3/2011 Foley et al.
7,900,524 B2 3/2011 Calloway et al.
7,907,166 B2 3/2011 Lamprecht et al.
7,909,122 B2 3/2011 Schena et al.
7,925,653 B2 4/2011 Saptharishi
7,930,065 B2 4/2011 Larkin et al.
7,935,130 B2 5/2011 Willliams
7,940,999 B2 5/2011 Liao et al.
7,945,012 B2 5/2011 Ye et al.
7,945,021 B2 5/2011 Shapiro et al.
7,953,470 B2 5/2011 Vetter et al.
7,954,397 B2 6/2011 Choi et al.
7,971,341 B2 7/2011 Dukesherer et al.
7,974,674 B2 7/2011 Hauck et al.
7,974,677 B2 7/2011 Mire et al.
7,974,681 B2 7/2011 Wallace et al.
7,979,157 B2 7/2011 Anvari
7,983,733 B2 7/2011 Viswanathan
7,988,215 B2 8/2011 Seibold
7,996,110 B2 8/2011 Lipow et al.
8,004,121 B2 8/2011 Sartor
8,004,229 B2 8/2011 Nowlin et al.
8,010,177 B2 8/2011 Csavoy et al.
8,019,045 B2 9/2011 Kato
8,021,310 B2 9/2011 Sanborn et al.
8,035,685 B2 10/2011 Jensen
8,046,054 B2 10/2011 Kim et al.
8,046,057 B2 10/2011 Clarke
8,052,688 B2 11/2011 Wolf, II
8,054,184 B2 11/2011 Cline et al.
8,054,752 B2 11/2011 Druke et al.
8,057,397 B2 11/2011 Li et al.
8,057,407 B2 11/2011 Martinelli et al.
8,062,288 B2 11/2011 Cooper et al.
8,062,375 B2 11/2011 Glerum et al.
8,066,524 B2 11/2011 Burbank et al.
8,073,335 B2 12/2011 Labonville et al.
8,079,950 B2 12/2011 Stern et al.
8,086,299 B2 12/2011 Adler et al.
8,092,370 B2 1/2012 Roberts et al.
8,098,914 B2 1/2012 Liao et al.
8,100,950 B2 1/2012 St. Clair et al.
8,105,320 B2 1/2012 Manzo
8,108,025 B2 1/2012 Csavoy et al.
8,109,877 B2 2/2012 Moctezuma de la Barrera et al.
8,112,292 B2 2/2012 Simon
8,116,430 B1 2/2012 Shapiro et al.
8,120,301 B2 2/2012 Goldberg et al.
8,121,249 B2 2/2012 Wang et al.
8,123,675 B2 2/2012 Funda et al.
8,133,229 B1 3/2012 Bonutti
8,142,420 B2 3/2012 Schena
8,147,494 B2 4/2012 Leitner et al.
8,150,494 B2 4/2012 Simon et al.
8,150,497 B2 4/2012 Gielen et al.
8,150,498 B2 4/2012 Gielen et al.
8,165,658 B2 4/2012 Waynik et al.
8,170,313 B2 5/2012 Kendrick et al.
8,179,073 B2 5/2012 Farritor et al.
8,182,476 B2 5/2012 Julian et al.
8,184,880 B2 5/2012 Zhao et al.
8,202,278 B2 6/2012 Orban, III et al.
8,208,708 B2 6/2012 Homan et al.
8,208,988 B2 6/2012 Jensen
8,219,177 B2 7/2012 Smith et al.
8,219,178 B2 7/2012 Smith et al.
8,220,468 B2 7/2012 Cooper et al.
8,224,024 B2 7/2012 Foxlin et al.
8,224,484 B2 7/2012 Swarup et al.
8,225,798 B2 7/2012 Baldwin et al.
8,228,368 B2 7/2012 Zhao et al.
8,231,610 B2 7/2012 Jo et al.
8,239,001 B2 8/2012 Verard et al.
8,241,271 B2 8/2012 Millman et al.
8,248,413 B2 8/2012 Gattani et al.
8,256,319 B2 9/2012 Cooper et al.
8,263,933 B2 9/2012 Zeile
8,271,069 B2 9/2012 Jascob et al.
8,271,130 B2 9/2012 Hourtash
8,281,670 B2 10/2012 Larkin et al.
8,282,653 B2 10/2012 Nelson et al.
8,301,226 B2 10/2012 Csavoy et al.
8,311,611 B2 11/2012 Csavoy et al.
8,320,991 B2 11/2012 Jascob et al.
8,332,012 B2 12/2012 Kienzle, III
8,333,755 B2 12/2012 Cooper et al.
8,335,552 B2 12/2012 Stiles
8,335,557 B2 12/2012 Maschke
8,348,931 B2 1/2013 Cooper et al.
8,353,963 B2 1/2013 Glerum
8,358,818 B2 1/2013 Miga et al.
8,359,730 B2 1/2013 Burg et al.
8,374,673 B2 2/2013 Adcox et al.
8,374,723 B2 2/2013 Zhao et al.
8,379,791 B2 2/2013 Forthmann et al.
8,386,019 B2 2/2013 Camus et al.
8,392,022 B2 3/2013 Ortmaier et al.
8,394,099 B2 3/2013 Patwardhan
8,395,342 B2 3/2013 Prisco
8,398,634 B2 3/2013 Manzo et al.
8,400,094 B2 3/2013 Schena
8,414,957 B2 4/2013 Enzerink et al.
8,418,073 B2 4/2013 Mohr et al.
8,450,694 B2 5/2013 Baviera et al.
8,452,447 B2 5/2013 Nixon
RE44,305 E 6/2013 Foley et al.
8,462,911 B2 6/2013 Vesel et al.
8,465,476 B2 6/2013 Rogers et al.
8,465,771 B2 6/2013 Wan et al.
8,467,851 B2 6/2013 Mire et al.
8,467,852 B2 6/2013 Csavoy et al.
8,469,947 B2 6/2013 Devengenzo et al.
RE44,392 E 7/2013 Hynes
8,483,434 B2 7/2013 Buehner et al.
8,483,800 B2 7/2013 Jensen et al.
8,486,532 B2 7/2013 Enzerink et al.
8,489,235 B2 7/2013 Moll et al.
8,500,722 B2 8/2013 Cooper
8,500,728 B2 8/2013 Newton et al.
8,504,201 B2 8/2013 Moll et al.
8,506,555 B2 8/2013 Ruiz Morales
8,506,556 B2 8/2013 Schena
8,508,173 B2 8/2013 Goldberg et al.
8,512,318 B2 8/2013 Tovey et al.
8,515,576 B2 8/2013 Lipow et al.
8,518,120 B2 8/2013 Glerum et al.
8,521,331 B2 8/2013 Itkowitz
8,526,688 B2 9/2013 Groszmann et al.
8,526,700 B2 9/2013 Isaacs

(56) References Cited

U.S. PATENT DOCUMENTS

| | | | |
|---|---|---|---|
| 8,527,094 | B2 | 9/2013 | Kumar et al. |
| 8,528,440 | B2 | 9/2013 | Morley et al. |
| 8,532,741 | B2 | 9/2013 | Heruth et al. |
| 8,541,970 | B2 | 9/2013 | Nowlin et al. |
| 8,548,563 | B2 | 10/2013 | Simon et al. |
| 8,549,732 | B2 | 10/2013 | Burg et al. |
| 8,551,114 | B2 | 10/2013 | Ramos de la Pena |
| 8,551,116 | B2 | 10/2013 | Julian et al. |
| 8,556,807 | B2 | 10/2013 | Scott et al. |
| 8,556,979 | B2 | 10/2013 | Glerum et al. |
| 8,560,118 | B2 | 10/2013 | Green et al. |
| 8,561,473 | B2 | 10/2013 | Blumenkranz |
| 8,562,594 | B2 | 10/2013 | Cooper et al. |
| 8,571,638 | B2 | 10/2013 | Shoham |
| 8,571,710 | B2 | 10/2013 | Coste-Maniere et al. |
| 8,573,465 | B2 | 11/2013 | Shelton, IV |
| 8,574,303 | B2 | 11/2013 | Sharkey et al. |
| 8,585,420 | B2 | 11/2013 | Burbank et al. |
| 8,594,841 | B2 | 11/2013 | Zhao et al. |
| 8,597,198 | B2 | 12/2013 | Sanborn et al. |
| 8,600,478 | B2 | 12/2013 | Verard et al. |
| 8,603,077 | B2 | 12/2013 | Cooper et al. |
| 8,611,985 | B2 | 12/2013 | Lavallee et al. |
| 8,613,230 | B2 | 12/2013 | Blumenkranz et al. |
| 8,621,939 | B2 | 1/2014 | Blumenkranz et al. |
| 8,624,537 | B2 | 1/2014 | Nowlin et al. |
| 8,630,389 | B2 | 1/2014 | Kato |
| 8,634,897 | B2 | 1/2014 | Simon et al. |
| 8,634,957 | B2 | 1/2014 | Toth et al. |
| 8,638,056 | B2 | 1/2014 | Goldberg et al. |
| 8,638,057 | B2 | 1/2014 | Goldberg et al. |
| 8,639,000 | B2 | 1/2014 | Zhao et al. |
| 8,641,726 | B2 | 2/2014 | Bonutti |
| 8,644,907 | B2 | 2/2014 | Hartmann et al. |
| 8,657,809 | B2 | 2/2014 | Schoepp |
| 8,660,635 | B2 | 2/2014 | Simon et al. |
| 8,666,544 | B2 | 3/2014 | Moll et al. |
| 8,675,939 | B2 | 3/2014 | Moctezuma de la Barrera |
| 8,678,647 | B2 | 3/2014 | Gregerson et al. |
| 8,679,125 | B2 | 3/2014 | Smith et al. |
| 8,679,183 | B2 | 3/2014 | Glerum et al. |
| 8,682,413 | B2 | 3/2014 | Lloyd |
| 8,684,253 | B2 | 4/2014 | Giordano et al. |
| 8,685,098 | B2 | 4/2014 | Glerum et al. |
| 8,693,730 | B2 | 4/2014 | Umasuthan et al. |
| 8,694,075 | B2 | 4/2014 | Groszmann et al. |
| 8,696,458 | B2 | 4/2014 | Foxlin et al. |
| 8,700,123 | B2 | 4/2014 | Okamura et al. |
| 8,706,086 | B2 | 4/2014 | Glerum |
| 8,706,185 | B2 | 4/2014 | Foley et al. |
| 8,706,301 | B2 | 4/2014 | Zhao et al. |
| 8,717,430 | B2 | 5/2014 | Simon et al. |
| 8,727,618 | B2 | 5/2014 | Maschke et al. |
| 8,734,432 | B2 | 5/2014 | Tuma et al. |
| 8,738,115 | B2 | 5/2014 | Amberg et al. |
| 8,738,181 | B2 | 5/2014 | Greer et al. |
| 8,740,882 | B2 | 6/2014 | Jun et al. |
| 8,746,252 | B2 | 6/2014 | McGrogan et al. |
| 8,749,189 | B2 | 6/2014 | Nowlin et al. |
| 8,749,190 | B2 | 6/2014 | Nowlin et al. |
| 8,761,930 | B2 | 6/2014 | Nixon |
| 8,764,448 | B2 | 7/2014 | Yang et al. |
| 8,771,170 | B2 | 7/2014 | Mesallum et al. |
| 8,781,186 | B2 | 7/2014 | Clements et al. |
| 8,781,630 | B2 | 7/2014 | Banks et al. |
| 8,784,385 | B2 | 7/2014 | Boyden et al. |
| 8,786,241 | B2 | 7/2014 | Nowlin et al. |
| 8,787,520 | B2 | 7/2014 | Baba |
| 8,792,704 | B2 | 7/2014 | Isaacs |
| 8,798,231 | B2 | 8/2014 | Notohara et al. |
| 8,800,838 | B2 | 8/2014 | Shelton, IV |
| 8,808,164 | B2 | 8/2014 | Hoffman et al. |
| 8,812,077 | B2 | 8/2014 | Dempsey |
| 8,814,793 | B2 | 8/2014 | Brabrand |
| 8,816,628 | B2 | 8/2014 | Nowlin et al. |
| 8,818,105 | B2 | 8/2014 | Myronenko et al. |
| 8,820,605 | B2 | 9/2014 | Shelton, IV |
| 8,821,511 | B2 | 9/2014 | Von Jako et al. |
| 8,823,308 | B2 | 9/2014 | Nowlin et al. |
| 8,827,996 | B2 | 9/2014 | Scott et al. |
| 8,828,024 | B2 | 9/2014 | Farritor et al. |
| 8,830,224 | B2 | 9/2014 | Zhao et al. |
| 8,834,489 | B2 | 9/2014 | Cooper et al. |
| 8,834,490 | B2 | 9/2014 | Bonutti |
| 8,838,270 | B2 | 9/2014 | Druke et al. |
| 8,844,789 | B2 | 9/2014 | Shelton, IV et al. |
| 8,855,822 | B2 | 10/2014 | Bartol et al. |
| 8,858,598 | B2 | 10/2014 | Seifert et al. |
| 8,860,753 | B2 | 10/2014 | Bhandarkar et al. |
| 8,864,751 | B2 | 10/2014 | Prisco et al. |
| 8,864,798 | B2 | 10/2014 | Weiman et al. |
| 8,864,833 | B2 | 10/2014 | Glerum et al. |
| 8,867,703 | B2 | 10/2014 | Shapiro et al. |
| 8,870,880 | B2 | 10/2014 | Himmelberger et al. |
| 8,876,866 | B2 | 11/2014 | Zappacosta et al. |
| 8,880,223 | B2 | 11/2014 | Raj et al. |
| 8,882,803 | B2 | 11/2014 | Iott et al. |
| 8,883,210 | B1 | 11/2014 | Truncale et al. |
| 8,888,821 | B2 | 11/2014 | Rezach et al. |
| 8,888,853 | B2 | 11/2014 | Glerum et al. |
| 8,888,854 | B2 | 11/2014 | Glerum et al. |
| 8,894,652 | B2 | 11/2014 | Seifert et al. |
| 8,894,688 | B2 | 11/2014 | Suh |
| 8,894,691 | B2 | 11/2014 | Iott et al. |
| 8,906,069 | B2 | 12/2014 | Hansell et al. |
| 8,964,934 | B2 | 2/2015 | Ein-Gal |
| 8,992,580 | B2 | 3/2015 | Bar et al. |
| 8,996,169 | B2 | 3/2015 | Lightcap et al. |
| 9,001,963 | B2 | 4/2015 | Sowards-Emmerd et al. |
| 9,002,076 | B2 | 4/2015 | Khadem et al. |
| 9,044,190 | B2 | 6/2015 | Rubner et al. |
| 9,107,683 | B2 | 8/2015 | Hourtash et al. |
| 9,125,556 | B2 | 9/2015 | Zehavi et al. |
| 9,131,986 | B2 | 9/2015 | Greer et al. |
| 9,215,968 | B2 | 12/2015 | Schostek et al. |
| 9,308,050 | B2 | 4/2016 | Kostrzewski et al. |
| 9,380,984 | B2 | 7/2016 | Li et al. |
| 9,393,039 | B2 | 7/2016 | Lechner et al. |
| 9,398,886 | B2 | 7/2016 | Gregerson et al. |
| 9,398,890 | B2 | 7/2016 | Dong et al. |
| 9,414,859 | B2 | 8/2016 | Ballard et al. |
| 9,420,975 | B2 | 8/2016 | Gutfleisch et al. |
| 9,492,235 | B2 | 11/2016 | Hourtash et al. |
| 9,592,096 | B2 | 3/2017 | Maillet et al. |
| 9,750,465 | B2 | 9/2017 | Engel et al. |
| 9,757,203 | B2 | 9/2017 | Hourtash et al. |
| 9,795,354 | B2 | 10/2017 | Menegaz et al. |
| 9,814,535 | B2 | 11/2017 | Bar et al. |
| 9,820,783 | B2 | 11/2017 | Donner et al. |
| 9,833,265 | B2 | 12/2017 | Donner et al. |
| 9,848,922 | B2 | 12/2017 | Tohmeh et al. |
| 9,925,011 | B2 | 3/2018 | Gombert et al. |
| 9,931,025 | B1 | 4/2018 | Graetzel et al. |
| 10,034,717 | B2 | 7/2018 | Miller et al. |
| 2001/0036302 | A1 | 11/2001 | Miller |
| 2002/0035321 | A1 | 3/2002 | Bucholz et al. |
| 2004/0068172 | A1 | 4/2004 | Nowinski et al. |
| 2004/0076259 | A1 | 4/2004 | Jensen et al. |
| 2005/0096502 | A1 | 5/2005 | Khalili |
| 2005/0143651 | A1 | 6/2005 | Verard et al. |
| 2005/0171558 | A1 | 8/2005 | Abovitz et al. |
| 2006/0100610 | A1 | 5/2006 | Wallace et al. |
| 2006/0173329 | A1 | 8/2006 | Marquart et al. |
| 2006/0184396 | A1 | 8/2006 | Dennis et al. |
| 2006/0241416 | A1 | 10/2006 | Marquart et al. |
| 2006/0291612 | A1 | 12/2006 | Nishide et al. |
| 2007/0015987 | A1 | 1/2007 | Benlloch Baviera et al. |
| 2007/0021738 | A1 | 1/2007 | Hasser et al. |
| 2007/0038059 | A1 | 2/2007 | Sheffer et al. |
| 2007/0073133 | A1 | 3/2007 | Schoenefeld |
| 2007/0156121 | A1 | 7/2007 | Millman et al. |
| 2007/0156157 | A1 | 7/2007 | Nahum et al. |
| 2007/0167712 | A1 | 7/2007 | Keglovich et al. |
| 2007/0233238 | A1 | 10/2007 | Huynh et al. |

(56) References Cited

U.S. PATENT DOCUMENTS

2008/0004523 A1 1/2008 Jensen
2008/0013809 A1 1/2008 Zhu et al.
2008/0033283 A1 2/2008 Dellaca et al.
2008/0046122 A1 2/2008 Manzo et al.
2008/0082109 A1 4/2008 Moll et al.
2008/0108912 A1 5/2008 Node-Langlois
2008/0108991 A1 5/2008 von Jako
2008/0109012 A1 5/2008 Falco et al.
2008/0144906 A1 6/2008 Allred et al.
2008/0161680 A1 7/2008 von Jako et al.
2008/0161682 A1 7/2008 Kendrick et al.
2008/0177203 A1 7/2008 von Jako
2008/0214922 A1 9/2008 Hartmann et al.
2008/0228068 A1 9/2008 Viswanathan et al.
2008/0228196 A1 9/2008 Wang et al.
2008/0235052 A1 9/2008 Node-Langlois et al.
2008/0269596 A1 10/2008 Revie et al.
2008/0287771 A1 11/2008 Anderson
2008/0287781 A1 11/2008 Revie et al.
2008/0300477 A1 12/2008 Lloyd et al.
2008/0300478 A1 12/2008 Zuhars et al.
2008/0302950 A1 12/2008 Park et al.
2008/0306490 A1 12/2008 Lakin et al.
2008/0319311 A1 12/2008 Hamadeh
2009/0012509 A1 1/2009 Csavoy et al.
2009/0030428 A1 1/2009 Omori et al.
2009/0080737 A1 3/2009 Battle et al.
2009/0185655 A1 7/2009 Koken et al.
2009/0198121 A1 8/2009 Hoheisel
2009/0216113 A1 8/2009 Meier et al.
2009/0228019 A1 9/2009 Gross et al.
2009/0259123 A1 10/2009 Navab et al.
2009/0259230 A1 10/2009 Khadem et al.
2009/0264899 A1 10/2009 Appenrodt et al.
2009/0281417 A1 11/2009 Hartmann et al.
2010/0022874 A1 1/2010 Wang et al.
2010/0039506 A1 2/2010 Sarvestani et al.
2010/0125286 A1 5/2010 Wang et al.
2010/0130986 A1 5/2010 Mailloux et al.
2010/0228117 A1 9/2010 Hartmann
2010/0228265 A1 9/2010 Prisco
2010/0249571 A1 9/2010 Jensen et al.
2010/0274120 A1 10/2010 Heuscher
2010/0280363 A1 11/2010 Skarda et al.
2010/0331858 A1 12/2010 Simaan et al.
2011/0022229 A1 1/2011 Jang et al.
2011/0077504 A1 3/2011 Fischer et al.
2011/0098553 A1 4/2011 Robbins et al.
2011/0137152 A1 6/2011 Li
2011/0213384 A1 9/2011 Jeong
2011/0224684 A1 9/2011 Larkin et al.
2011/0224685 A1 9/2011 Larkin et al.
2011/0224686 A1 9/2011 Larkin et al.
2011/0224687 A1 9/2011 Larkin et al.
2011/0224688 A1 9/2011 Larkin et al.
2011/0224689 A1 9/2011 Larkin et al.
2011/0224825 A1 9/2011 Larkin et al.
2011/0230967 A1 9/2011 O'Halloran et al.
2011/0238080 A1 9/2011 Ranjit et al.
2011/0276058 A1 11/2011 Choi et al.
2011/0282189 A1 11/2011 Graumann
2011/0286573 A1 11/2011 Schretter et al.
2011/0295062 A1 12/2011 Solsona et al.
2011/0295370 A1 12/2011 Suh et al.
2011/0306986 A1 12/2011 Lee et al.
2012/0035507 A1 2/2012 George et al.
2012/0046668 A1 2/2012 Gantes
2012/0051498 A1 3/2012 Koishi
2012/0053597 A1 3/2012 Anvari et al.
2012/0059248 A1 3/2012 Holsing et al.
2012/0071753 A1 3/2012 Hunter et al.
2012/0108954 A1 5/2012 Schulhauser et al.
2012/0136372 A1 5/2012 Amat Girbau et al.
2012/0143084 A1 6/2012 Shoham
2012/0184839 A1 7/2012 Woerlein
2012/0197182 A1 8/2012 Millman et al.
2012/0226145 A1 9/2012 Chang et al.
2012/0235909 A1 9/2012 Birkenbach et al.
2012/0245596 A1 9/2012 Meenink
2012/0253332 A1 10/2012 Moll
2012/0253360 A1 10/2012 White et al.
2012/0256092 A1 10/2012 Zingerman
2012/0294498 A1 11/2012 Popovic
2012/0296203 A1 11/2012 Hartmann et al.
2013/0006267 A1 1/2013 Odermatt et al.
2013/0016889 A1 1/2013 Myronenko et al.
2013/0030571 A1 1/2013 Ruiz Morales et al.
2013/0035583 A1 2/2013 Park et al.
2013/0060146 A1 3/2013 Yang et al.
2013/0060337 A1 3/2013 Petersheim et al.
2013/0094742 A1 4/2013 Feilkas
2013/0096574 A1 4/2013 Kang et al.
2013/0113791 A1 5/2013 Isaacs et al.
2013/0116706 A1 5/2013 Lee et al.
2013/0131695 A1 5/2013 Scarfogliero et al.
2013/0144307 A1 6/2013 Jeong et al.
2013/0158542 A1 6/2013 Manzo et al.
2013/0165937 A1 6/2013 Patwardhan
2013/0178867 A1 7/2013 Farritor et al.
2013/0178868 A1 7/2013 Roh
2013/0178870 A1 7/2013 Schena
2013/0204271 A1 8/2013 Brisson et al.
2013/0211419 A1 8/2013 Jensen
2013/0211420 A1 8/2013 Jensen
2013/0218142 A1 8/2013 Tuma et al.
2013/0223702 A1 8/2013 Holsing et al.
2013/0225942 A1 8/2013 Holsing et al.
2013/0225943 A1 8/2013 Holsing et al.
2013/0231556 A1 9/2013 Holsing et al.
2013/0237995 A1 9/2013 Lee et al.
2013/0245375 A1 9/2013 DiMaio et al.
2013/0261640 A1 10/2013 Kim et al.
2013/0272488 A1 10/2013 Bailey et al.
2013/0272489 A1 10/2013 Dickman et al.
2013/0274761 A1 10/2013 Devengenzo et al.
2013/0281821 A1 10/2013 Liu et al.
2013/0296884 A1 11/2013 Taylor et al.
2013/0303887 A1 11/2013 Holsing et al.
2013/0307955 A1 11/2013 Deitz et al.
2013/0317521 A1 11/2013 Choi et al.
2013/0325033 A1 12/2013 Schena et al.
2013/0325035 A1 12/2013 Hauck et al.
2013/0331686 A1 12/2013 Freysinger et al.
2013/0331858 A1 12/2013 Devengenzo et al.
2013/0331861 A1 12/2013 Yoon
2013/0342578 A1 12/2013 Isaacs
2013/0345717 A1 12/2013 Markvicka et al.
2013/0345757 A1 12/2013 Stad
2014/0001235 A1 1/2014 Shelton, IV
2014/0012131 A1 1/2014 Heruth et al.
2014/0031664 A1 1/2014 Kang et al.
2014/0046128 A1 2/2014 Lee et al.
2014/0046132 A1 2/2014 Hoeg et al.
2014/0046340 A1 2/2014 Wilson et al.
2014/0049629 A1 2/2014 Siewerdsen et al.
2014/0058406 A1 2/2014 Tsekos
2014/0073914 A1 3/2014 Lavallee et al.
2014/0080086 A1 3/2014 Chen
2014/0081128 A1 3/2014 Verard et al.
2014/0088612 A1 3/2014 Bartol et al.
2014/0094694 A1 4/2014 Moctezuma de la Barrera
2014/0094851 A1 4/2014 Gordon
2014/0096369 A1 4/2014 Matsumoto et al.
2014/0100587 A1 4/2014 Farritor et al.
2014/0121676 A1 5/2014 Kostrzewski et al.
2014/0128882 A1 5/2014 Kwak et al.
2014/0130810 A1 5/2014 Azizian et al.
2014/0135796 A1 5/2014 Simon et al.
2014/0142591 A1 5/2014 Alvarez et al.
2014/0142592 A1 5/2014 Moon et al.
2014/0148692 A1 5/2014 Hartmann et al.
2014/0163581 A1 6/2014 Devengenzo et al.
2014/0171781 A1 6/2014 Stiles
2014/0171900 A1 6/2014 Stiles

(56) References Cited

U.S. PATENT DOCUMENTS

2014/0171965 A1 6/2014 Loh et al.
2014/0180308 A1 6/2014 von Grunberg
2014/0180309 A1 6/2014 Seeber et al.
2014/0187915 A1 7/2014 Yaroshenko et al.
2014/0188132 A1 7/2014 Kang
2014/0194699 A1 7/2014 Roh et al.
2014/0221819 A1 8/2014 Sarment
2014/0222023 A1 8/2014 Kim et al.
2014/0228631 A1 8/2014 Kwak et al.
2014/0234804 A1 8/2014 Huang et al.
2014/0257328 A1 9/2014 Kim et al.
2014/0257329 A1 9/2014 Jang et al.
2014/0257330 A1 9/2014 Choi et al.
2014/0275760 A1 9/2014 Lee et al.
2014/0275985 A1 9/2014 Walker et al.
2014/0276931 A1 9/2014 Parihar et al.
2014/0276940 A1 9/2014 Seo
2014/0276944 A1 9/2014 Farritor et al.
2014/0288413 A1 9/2014 Hwang et al.
2014/0299648 A1 10/2014 Shelton, IV et al.
2014/0303434 A1 10/2014 Farritor et al.
2014/0303643 A1 10/2014 Ha et al.
2014/0305995 A1 10/2014 Shelton, IV et al.
2014/0309659 A1 10/2014 Roh et al.
2014/0316436 A1 10/2014 Bar et al.
2014/0323803 A1 10/2014 Hoffman et al.
2014/0324070 A1 10/2014 Min et al.
2014/0330288 A1 11/2014 Date et al.
2014/0364720 A1 12/2014 Darrow et al.
2014/0371577 A1 12/2014 Maillet et al.
2015/0039034 A1 2/2015 Frankel et al.
2015/0085970 A1 3/2015 Bouhnik et al.
2015/0146847 A1 5/2015 Liu
2015/0150524 A1 6/2015 Yorkston et al.
2015/0196261 A1 7/2015 Funk
2015/0213633 A1 7/2015 Chang et al.
2015/0335480 A1 11/2015 Alvarez et al.
2015/0342647 A1 12/2015 Frankel et al.
2016/0005194 A1 1/2016 Schretter et al.
2016/0166329 A1 6/2016 Langan et al.
2016/0235480 A1 8/2016 Scholl et al.
2016/0249990 A1 9/2016 Glozman et al.
2016/0302871 A1 10/2016 Gregerson et al.
2016/0320322 A1 11/2016 Suzuki
2016/0331335 A1 11/2016 Gregerson et al.
2017/0135770 A1 5/2017 Scholl et al.
2017/0143284 A1 5/2017 Sehnert et al.
2017/0143426 A1 5/2017 Isaacs et al.
2017/0156816 A1 6/2017 Ibrahim
2017/0202629 A1 7/2017 Maillet et al.
2017/0212723 A1 7/2017 Atarot et al.
2017/0215825 A1 8/2017 Johnson et al.
2017/0215826 A1 8/2017 Johnson et al.
2017/0215827 A1 8/2017 Johnson et al.
2017/0231710 A1 8/2017 Scholl et al.
2017/0258426 A1 9/2017 Risher-Kelly et al.
2017/0273748 A1 9/2017 Hourtash et al.
2017/0296277 A1 10/2017 Hourtash et al.
2017/0360493 A1 12/2017 Zucher et al.

COMPUTER ASSISTED SURGERY NAVIGATION MULTI-POSTURE IMAGING BASED KINEMATIC SPINE MODEL

FIELD

The present disclosure relates to medical devices and systems, and more particularly, providing navigation information to surgeons and/or surgical robots for computer assisted navigation during spinal surgery.

BACKGROUND

There are a numerous types of spinal surgery procedures, including vertebroplasty and kyphoplasty, spinal laminectomy or spinal decompression, discectomy, foraminotomy, spinal fusion, and disk replacement. Patient satisfaction with the outcome of spinal surgery can depend upon the surgeon's expertise with best practices and use of rapidly emerging innovations in surgical procedures, new and customized implant designs, computer-assisted navigation, and surgical robot systems.

For example, the postoperative outcome for patient from spinal surgery can be improved through interoperative actions which incise, dissect, or otherwise disturb patient anatomy only to the extent defined by a surgical plan. Failure to do so may result in iatrogenic pathologies and unwanted complications. It is therefore beneficial to fully understand the biological components of the anatomy at a surgical site. Currently, preoperative and/or intraoperative imaging can be provided to surgeons to help navigate surgery procedures and enable more direct visualization of the intraoperative progress of the surgery. Image based navigation may be used in conjunction with robotic navigation to perform a surgical procedure. These navigation approaches can be subject to limitations which should be addressed to reduce unnecessary disturbance of patient anatomy during surgery on the spine.

SUMMARY

Some embodiments of the present disclosure are directed to a surgical planning system to provide computer assisted navigation for spinal surgery. The surgical planning system includes a computer platform that is operative to obtain images of at least two different postures of a patient's spine, and to measure displacement of anatomical features of the patient's spine between the images of the at least two different postures of the patient's spine. The computer platform is further operative to estimate stiffness of the patient's spine based on the measurements of displacement, to generate a patient-specific kinematic model of the patient's spine based on the estimated stiffness, and to provide a surgical plan based on the patient-specific kinematic model of the patient's spine.

Some other embodiments are directed to corresponding methods by a surgical planning system to provide computer assisted navigation for spinal surgery. Some other embodiments are directed to corresponding computer program products for a surgical planning system to provide computer assisted navigation for spinal surgery.

Other surgical planning systems, methods, and computer program products according to embodiments will be or become apparent to one with skill in the art upon review of the following drawings and detailed description. It is intended that all such surgical planning systems, methods, and computer program products be included within this description, be within the scope of the present disclosure, and be protected by the accompanying claims. Moreover, it is intended that all embodiments disclosed herein can be implemented separately or combined in any way and/or combination.

BRIEF DESCRIPTION OF THE DRAWINGS

The accompanying drawings, which are included to provide a further understanding of the disclosure and are incorporated in a constitute a part of this application, illustrate certain non-limiting embodiments of inventive concepts. In the drawings.

DETAILED DESCRIPTION

Inventive concepts will now be described more fully hereinafter with reference to the accompanying drawings, in which examples of embodiments of inventive concepts are shown. Inventive concepts may, however, be embodied in many different forms and should not be construed as limited to the embodiments set forth herein. Rather, these embodiments are provided so that this disclosure will be thorough and complete, and will fully convey the scope of various present inventive concepts to those skilled in the art. It should also be noted that these embodiments are not mutually exclusive. Components from one embodiment may be tacitly assumed to be present or used in another embodiment.

Spine kinematics depend on a variety of parameters including patients' age, sex, anatomy and pathological conditions. The biomechanical and geometrical properties of spine govern the kinematics and are needed for biomechanical modeling and predictive surgical planning. Although innovative surgical tools and robotic navigation have significantly improved the outcome of spine surgery, mechanical failure rate should continue to be improved.

In accordance with various presently disclosed embodiments, a surgical plan is adapted based on the patient's diagnosis and demographics, and moreover adapted based on prediction of the postop alignment and overall outcome of the surgery. Understanding the stiffness of the spine during preoperative planning is a key constraint to achieving desired improvements but has previously been difficult to determine. The fundamental biomechanics of soft tissue are complicated in nature and are usually tested in cadavers or ex vivo tissues. Independent studies have typically lacked the ability to encompass a sufficiently relevant spectrum of patient variations and employ diverse methodologies, leading to challenges to conducting a meta-analysis.

The present disclosure provides operational embodiments that analyze multimodal patient images and/or multi-posture patient images which can be obtained through a uniform operational workflow of imaging guidelines and processes. Computer operations estimate the flexibility and anatomical features of a patient's spine from inputted spine images of the patient at different defined postures. Computer operations correlate stiffness of the spine with flexibility, and further use information from biomechanical studies to extrapolate the results to generate or adapt a predicted surgically modified spine model. Computer operations construct a patient-specific kinematic model based on the stiffness and anatomical features of the spine. Using a surgeon's (or other user's) input fixation plan or other spine surgery plan, computer operations use the kinematic model to estimate the forces (e.g., force vectors and locations of force application) which need to be applied intraoperatively to achieve a certain postoperative correction of the spine.

Figure 1:
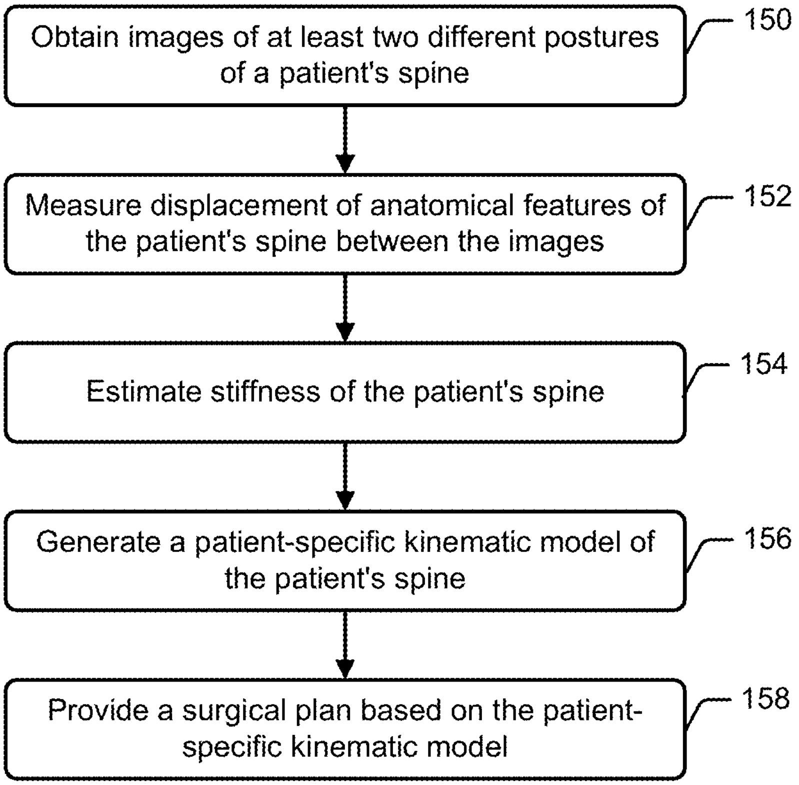
FIG. 1 illustrates computer operations that can be performed by a computer platform of a surgical planning system to provide computer assisted navigation for spinal surgery in accordance with some embodiments.
Figure 2:
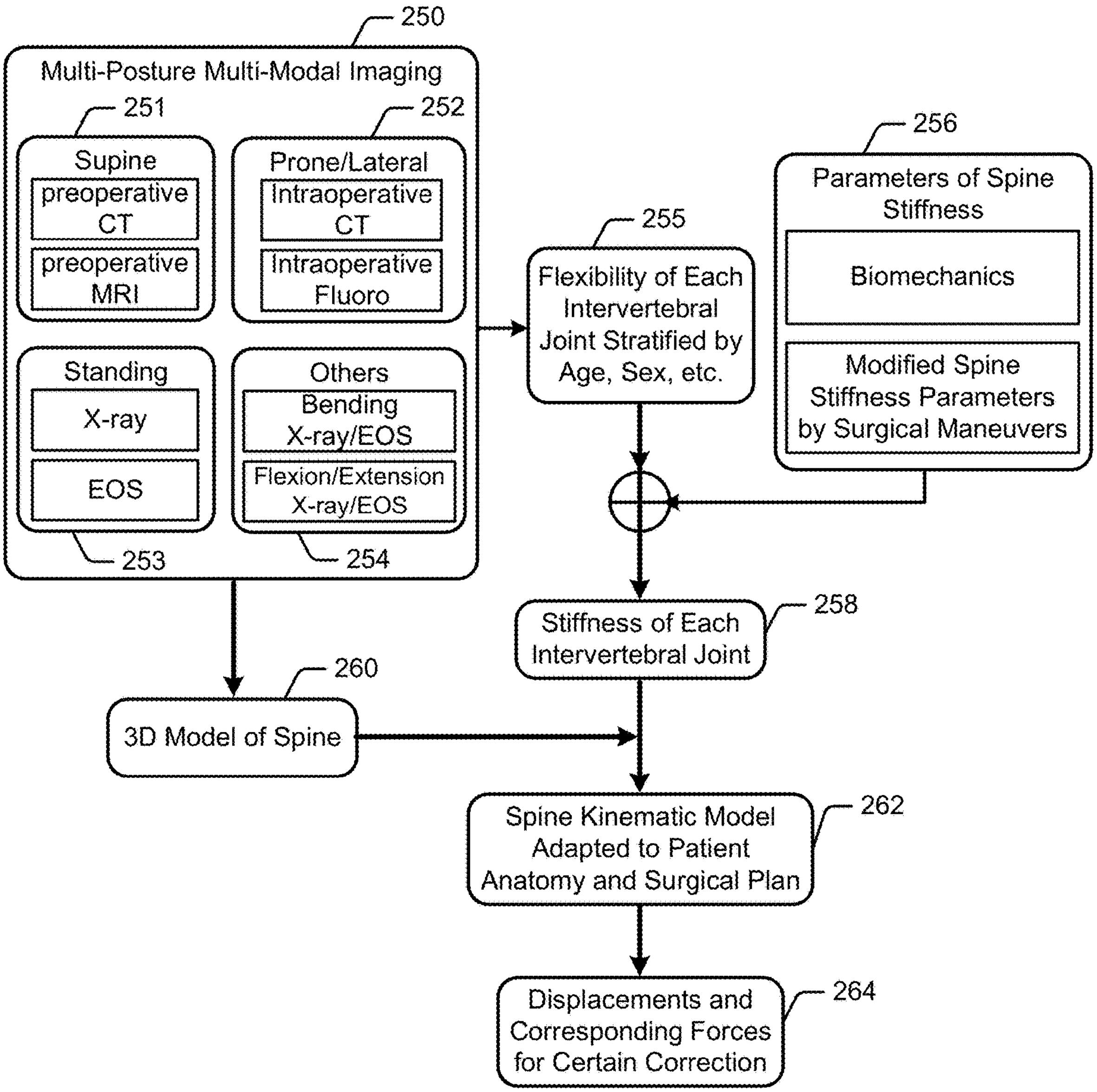
FIG. 2 illustrates more detailed example computer operations that can be performed by a computer platform for some of the operations illustrated in FIG. 1 in accordance with some embodiments.

These and other embodiments are initially discussed in the context of the example flowcharts of FIGS. 1 and 2. FIG. 1 illustrates computer operations that can be performed by a computer platform of a surgical planning system to provide computer assisted navigation for spinal surgery. FIG. 2 illustrates more detailed example computer operations that can be performed by a computer platform for some of the operations illustrated in FIG. 1 in accordance with some embodiments.

Referring initially to FIG. 1, operations by the computer platform include obtaining 150 images of at least two different postures of a patient's spine. The operations measure 152 displacement of anatomical features of the patient's spine between the images of the at least two different postures of the patient's spine. The measurements may include measuring the displacement of vertebral body centers and intervertebral disc centers of the patient's spine between the images of the at least two different postures of the patient's spine. The operations estimate 154 stiffness of the patient's spine based on the measurements of displacement. The operations generate 156 a patient-specific kinematic model of the patient's spine based on the estimated stiffness, and generate 158 a surgical plan based on the patient-specific kinematic model of the patient's spine. The surgical plan may be used to provide computer assistance during pre-operative planning of surgery, used to provide navigation during surgery, and/or used to control a surgical robot during surgery, such as described in further detail below. The surgical plan may be recorded on paper and/or output as digital data that can be provided to a preoperative planning component, intraoperative guidance component, and/or other components as discussed below with regard to FIG. 3.

As will be explained in further detail below, stiffness of the patient's spine is determined through the measurements of displacement of the anatomical features of the patient's spine as imaged in at least two different postures. The stiffness is then used to generate the patient-specific kinetic model which, in turn, is used to generate the surgical plan. As will be explained in detail below, the computer automated process can be applied more consistently across surgical plans for any patients to improve surgical outcomes, and can be adapted over time, e.g., through supervised machine learning from feedback, to more accurately generate patient-specific kinematic models.

Reference is now further made to the more detailed example operations shown in FIG. 2. The images can be obtained from a set 250 of multi-posture images which can be from multi-modal imaging techniques and devices. Example multi-posture multi-modal images in the set 250 can include one or more of: a subset 251 of preoperative computerized tomography (CT) images and/or preoperative magnetic resonance imaging (MRI) images of the patient's spine in a supine posture; a subset 252 of intraoperative CT and/or intraoperative fluoroscopy images of the patient's spine in a prone posture and/or lateral posture; a subset 253 of x-ray images and/or EOS (low-dose, weight-bearing X-ray) images of the patient's spine in a standing posture; and/or a subset 254 of other imaging modalities which may include x-ray and/or EOS images of the patient's spine in a bending posture, a flexion posture, and/or extension posture.

In some multi-image modality directed embodiments, the operation to measure 152 (FIG. 1) and 255 (FIG. 2) displacement of anatomical features of the patient's spine includes to measure the displacement of anatomical features of the patient's spine between images obtained by at least two different imaging modalities among a group of: CT imaging; MRI; Cone Beam Computerized Tomography (CBCT) imaging; Micro Computerized Tomography (MCT) imaging; 3D ultrasound imaging, x-ray imaging, and fluoroscopy imaging. The measured displacement may indicate distances that defined ones of the anatomical features have moved in a coordinate system of the 2D images or in 3D images and/or distances in another coordinate system (e.g., determined based on projecting the movements from the image coordinate system to other coordinate system).

The displacement measurements can indicate flexibility of each interverbal joint, and may be stratified by age, gender, etc.

In some multi-posture directed embodiments, the operation to measure 152 (FIG. 1) and 255 (FIG. 2) displacement of anatomical features of the patient's spine includes to measure the displacement of anatomical features of the patient's spine between at least two different ones of: a supine posture image of the patient's spine; a prone posture image of the patient's spine; a standing posture image of the patient's spine; a lateral posture image of the patient's spine; a standing posture image of the patient's spine; and a bending posture image of the patient's spine.

In a further embodiment, the measurement 152 (FIG. 1) and 255 (FIG. 2) of displacement of anatomical features of the patient's spine includes to measure the displacement of anatomical features of the patient's spine between a first image and a second image, where the first image is based on a preoperative CT or a preoperative MRI image of the patient's spine in one of a supine posture and a prone posture, and where the second image is based on an intraoperative CT image or an intraoperative fluoroscopy image of the patient's spine in the other one of the supine posture and the prone posture.

The measurement 152 (FIG. 1) and 255 (FIG. 2) of displacement of anatomical features of the patient's spine can include to measure the displacement of vertebral body centers and intervertebral disc centers of the patient's spine between the images of the at least two different postures of the patient's spine.

A 3D model of the patient's spine is generated 260 from any of the input image(s) by registration with a baseline spine model (e.g., statistical shape model of a spine). The same baseline spine model (e.g., statistical shape model) may be used for any of the imaging modalities, but may be adapted (tuned) using a registration algorithm based on characteristics of the particular imaging modality of the input image(s). This approach may ensure that the anatomical features of spine, including vertebral body centers, intervertebral disc centers, spinal processes, etc., are carried over to the patient-specific 3D spine model in a similar way for all imaging modalities.

Thus, in some embodiments, generation 260 of the 3D model of the patient's spine includes registering the anatomical features of the patient's spine imaged in at least one of the images to corresponding anatomical features of a baseline spine defined by a baseline spine model. The same baseline spine model may be used for all of the imaging modalities or the model may be selected from among a set of baseline spine models in a repository based on patient specific information (e.g., age, sex, etc.), based on similarity to the imaged anatomical features of the patient's spine to corresponding anatomical features of each of the baseline spine models, etc.

Flexibility of each intervertebral joint is estimated 255 based on the relative displacements in any two or more of the postures. Stiffness of intervertebral joint that governs the force displacement relationship is estimated 258 by correlating patient's spine flexibility (as indicated by the measured displacement) with baseline parameters of spine stiffness 256, which may be defined through biomechanical studies. The baseline parameters of spine stiffness 256 may define biomechanical relationships between the anatomical features of baseline spines (e.g., stiffness of intervertebral joints) measured through studies, e.g., cadavers, postoperative patient feedback, etc.) and may define modified spine stiffness parameters which are correlated to different defined surgical maneuvers of anatomical features of baseline spines. Operations for correlating the patient's spine flexibility with the baseline parameters of spine stiffness 256, may include to correlate the patient's spine flexibility to one of a set of defined baseline parameters categories, where the set of baseline parameters categories may include baseline parameters for normal flexibility observed in studies, other baseline parameters for hypo-flexibility observed in studies, and still other baseline parameters for hyper-flexibility observed in studies.

A patient-specific kinematic model of the spine is generated 156 (FIG. 1) and 262 (FIG. 2) based on the stiffness estimate 258 for the patient's spine. In some embodiments, the patient-specific kinematic model is generated based on combining the 3D model of the patient's spine and the stiffness parameters. The patient-specific kinematic model is thereby adapted to the specific patient measured parameters, and is further adapted and used for a spine surgery plan for the patient as discussed below. Also as discussed below, the patient-specific kinematic model of the patient's spine can operationally define relationships between levels of force applied to anatomical features of the 3D model of the patient's spine to resulting displacement of the anatomical features, which can be used to determine 264 what displacements and corresponding forces are needed through the surgery plan to obtain certain corrective outcomes for the patient's spine.

In some embodiments, the operation to estimate 154 (FIG. 1) and 258 (FIG. 2) stiffness of the patient's spine based on the measurements of displacement, includes to determine flexibility of intervertebral joints of the patient's spine based on the measurements of displacement of the intervertebral joints of the patient's spine between the images of the at least two different postures of the patient's spine. The operations obtain baseline biomechanical stiffness parameters of corresponding intervertebral joints of a baseline spine defined by a baseline spine model, and then estimate the stiffness of the intervertebral joints of the patient's spine based on correlating the determined flexibility of the intervertebral joints of the patient's spine to the baseline biomechanical stiffness parameters of the corresponding intervertebral joints of the baseline spine defined by the baseline spine model.

In some further embodiments, the operation to generate 156 (FIG. 1) and 262 (FIG. 2) the patient-specific kinematic model of the patient's spine based on the estimated stiffness, includes to generate a 3D model of the patient's spine based on registering the anatomical features of the patient's spine imaged in at least one of the images to corresponding anatomical features of the baseline spine defined by the baseline spine model. The operations then generate the patient-specific kinematic model of the patient's spine using the estimate of the stiffness of the intervertebral joints of the patient's spine to operationally define relationships between levels of force applied to anatomical features of the 3D model of the patient's spine to resulting displacement of the anatomical features.

The surgical plan can then be generated 158 (FIG. 1) and 264 (FIG. 2) through operations that include to obtain a target displacement of at least one anatomical feature of the patient's spine, and estimate using the patient-specific kinematic model a level of force to be applied to at least one location on the patient's spine to obtain the target displacement of the at least one anatomical feature of the patient's spine. The surgical plan may be used to influence planning and/or actions by a surgeon and/or automated control of a computerized surgical process. For example, the surgical plan may be used to influence bending of a rod shape for spinal implant, selection of locations for spinal implants (e.g., screw placement, interbody spacer sizing and placement, etc.), osteotomy, etc.

Alternatively or additionally, the surgical plan can be generated 158 (FIG. 1) and 264 (FIG. 2) through operations that obtain a targeted displacement of anatomical features of the patient's spine through fixation of an implant to the patient's spine, and estimate using the patient-specific kinematic model a level of force that will be exerted on a surgical implant when used to fixate anatomical features of the patient's spine at the targeted displacement.

An example of the force estimation can include to estimate a level of force exerted on a particular pedicle screw or other implant to secure a spine fixation implant to fixate anatomical features of the patient's spine at the targeted displacement defined by the surgical plan. Such force estimation can enable a surgeon to assess the risk of a pedicle screw or other implant being subjected to excessive force (stress) and becoming dislodged or loose if embedded according to a candidate surgical plan.

The patient-specific kinematic model of the patient's spine may be generated using a machine learning model, such as the machine learning model 400 of a machine learning processing circuit 316 which is described below with regarding to FIGS. 3 and 4. In some embodiments, the operations to generate 156 (FIG. 1) and 262 (FIG. 2) the patient-specific kinematic model of the patient's spine based on the estimated stiffness, can include to process the images of the at least two different postures of the patient's spine through the machine learning model 400 of the machine learning processing circuit 316 (FIGS. 3 and 4) to generate a function relating inputted levels of force to be applied to anatomical features of the patient's spine to outputted resulting displacement of the anatomical features. The machine learning model 400 is trained to relate displacement of intervertebral joints of spines between the images of the at least two different postures of the patient's spine to stiffness of the intervertebral joints of the patient's spine.

The computer platform can provide computer assisted navigation data (158 in FIGS. 1 and 264 in FIG. 2) based on the surgical plan to a display device for preoperative surgery planning and/or intraoperative assisted surgery navigation on the patient's spine. The process for intraoperative assisted surgery navigation can include operations to determine a target displacement of at least one anatomical feature of the patient's spine based on the surgical plan (158 in FIGS. 1 and 264 in FIG. 2). The operations can obtain tool tracking data indicating pose of a tool relative to the patient's spine, such as by using one or more of the processes described below with regard to FIGS. 6-8, for tracking reference elements attached to tool(s) and other objects. The operations obtain spine tracking data indicating pose of the at least one anatomical feature of the patient's spine, e.g., using patient reference element(s) attached to the spine which are tracked by tracking cameras as discussed below. The operations process the tool tracking data, the spine tracking data, and the target displacement of the at least one anatomical feature of the patient's spine to generate intraoperative navigated guidance data. The operations can display the intraoperative navigated guidance data, e.g., on a head mounted display or other display device, to guide a user's movement of the tool.

Figure 6:
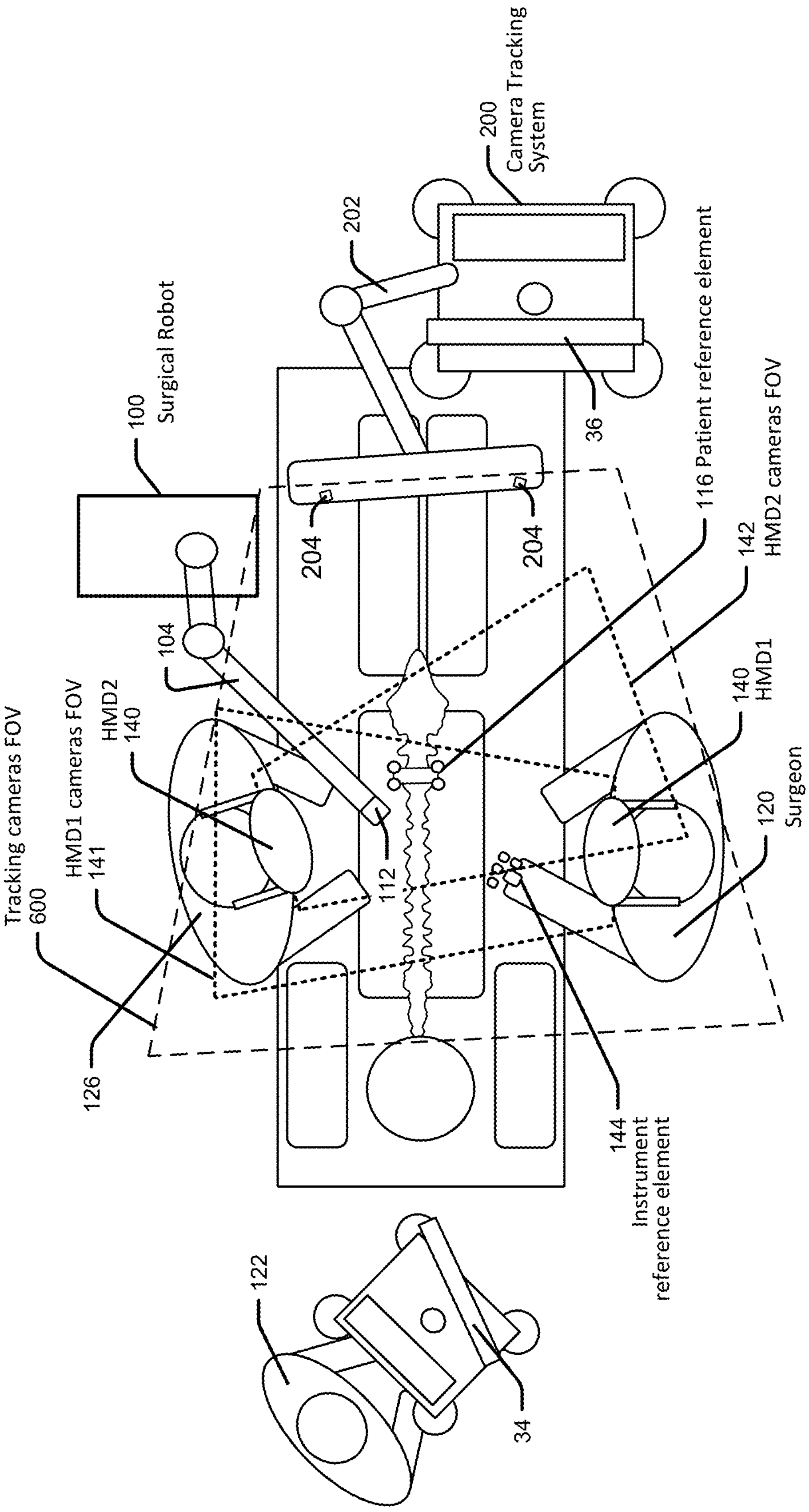
FIG. 6 illustrates an overhead view of a surgical system arranged during a surgical procedure in a surgical room which includes a camera tracking system for computer assisted navigation during surgery and which may further include a surgical robot for robotic assistance according to some embodiments.
Figure 7:
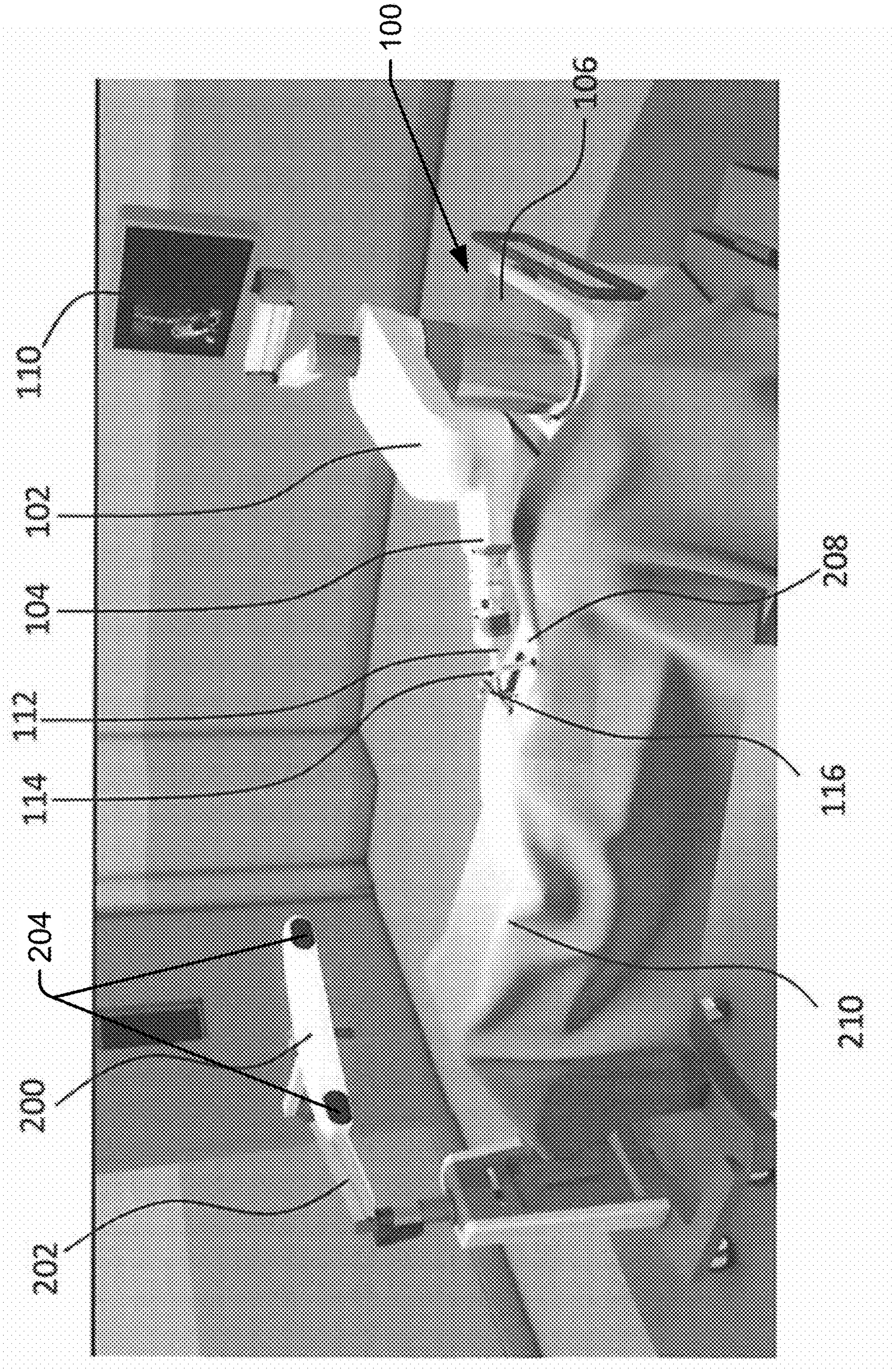
FIG. 7 illustrates the camera tracking system and the surgical robot positioned relative to a patient according to some embodiments.

Alternatively or additionally, the operations can provide computer assisted navigation data based on the surgical plan to a surgical robot 100 (FIGS. 6-8) to control movement of an end-effector 112 (FIGS. 6-8) of the surgical robot for computer assisted navigation during surgery on the patient's spine. The surgical navigation system can further include the surgical robot 100 which can be configured as shown in FIG. 7 to include a robot base 106, a robot arm 104 connected between the robot base 106 and an end effector 112. At least one motor is operatively connected to control movement of the end effector 112 via the robot arm 104 relative to the robot base 106. The computer platform is further operative to determine a target displacement of at least one anatomical feature of the patient's spine based on the computer assisted navigation data. The computer platform obtains tool tracking data indicating pose of a tool relative to the patient's spine, and obtains spine tracking data indicating pose of the at least one anatomical feature of the patient's spine. The computer platform processes the tool tracking data, the spine tracking data, and the target displacement of the at least one anatomical feature of the patient's spine to generate intraoperative navigated guidance data. The computer platform controls movement of the at least one motor based on the intraoperative navigated guidance data to guide movement of the tool.

Example questions and problems that exist in current lumbar interbody fusion procedures and other spinal surgery procedures include: how to make surgical procedures be patient specific but also standardized across patients; what is the targeted correction needed for best patient outcome based on presentation; and how much direct decompression is needed versus how much indirect decompression is needed.

There are multiple technique combinations and solutions for the same patient presentation, and there is variance among surgeons on which technique or approach would be chosen for the best patient outcome. This results in some variation in actual patient outcomes.

Embodiments of the present disclosure can address various of these questions and problems, by streamlining planning and surgical workflows, and identifying and using correlations to standardize patient outcomes. Some embodiments are directed to using integrated spine models which may be generated or adapted using supervised machine learning from preoperative, intraoperative, and/or postoperative feedback.

Some embodiments of the present disclosure are directed to surgical planning systems for computer assisted navigation during spinal surgery. The system processes numerous different types of inputs and continued data collection using artificial intelligence through machine learning models to find correlations between different patient presentations and their outcomes, cause and effect of various spine surgery elements (direct vs indirect decompression and degree of either, different approaches, actual amount of correction achieved per technique and implants used, etc.) to continually optimize AI-assisted spine surgery plans for better patient outcomes.

To establish a spine model and predictive algorithm to further support surgeon decision making in lumbar interbody fusion surgery, and improve patient outcomes, data is needed from multiple sources as first an initial baseline, and then to continually update and improve the spine model with machine learning.

Key points and planes of anatomy (e.g. pedicle cross sections, canal perimeters, foraminal heights, facet joints, superior/inferior endplates, intervertebral discs, vertebral body landmarks, etc.) derived from specific patient image scans, are used to generate a segmented spine model that can be used to auto-calculate preoperative spinal alignment parameters. In addition, preoperative data collection from literature, studies, physician key opinion leaders, existing electronic health records can be combined with other data obtained from the patient's scans (e.g. bone density, spine stiffness, etc.) to compile all the factors for input to determine the best path forward in terms of surgical intervention. With these inputs and continually trained spine models, the system can draw correlations between patients and outcomes. Examples of data that can be collected as inputs and derived during the preoperative stages are discussed below.

The surgical planning systems include a computer platform that executes computer software to perform operations that can accurately detect key points of anatomy derived from specific patient scans. The computer platform may comprise one or more processors which may be connected to a same backplane, multiple interconnected backplanes, or distributed across networked platforms. The computer software may generate a segmented spine model that can be used to calculate preoperative spinal alignment parameters, and (through machine learning, anatomical standards, pre/intra/post-operative data collection, and known patient outcomes) generate a machine learning model that can provide predictive surgical outcomes for a defined patient.

The predictive surgical outcomes can have sufficient accuracy to be relied upon for determining or suggesting possible diagnoses and/or determining ideal surgery access approach(es), degree of decompression needed (indirect and/or direct), required interbody size/placement, custom interbody expansion set points (height and lordosis), and fixation type/size/placement that would be required for the most ideal spinal correction and patient outcomes. The need for this type of capability ranges from complex spinal deformity cases to single level degenerative spinal cases, e.g., Interlaminar Lumbar Instrumented Fusion (ILIF) procedure, and may be beneficial for numerous types of spinal correction surgery including vertebral body replacements and disc replacements.

In some embodiments, the computer software accesses patient data in electronic health records (EHR) to operate to establish baseline data for a spine model for the patient. Patient data contained in an EHR may include, but is not limited to, patient demographics, patient medical history, diagnoses, medications, patient scans, lab results, and doctor's notes. The computer software may utilize machine learning model algorithms and operations for preoperative (preop) and/or intraoperative (intraop) surgical planning. These operations can reduce user input needed to set up patient profiles, and allow for continual seamless data synchronization.

This and other operational functionality can be provided by a surgical planning system for computer assisted navigation during spinal surgery. In accordance with some embodiments, the surgical planning system includes a computer platform that is operative to obtain intraoperative feedback data and/or postoperative feedback data regarding spinal surgery outcome for a plurality of patients, and to train a machine learning model based on the intraoperative feedback data and/or the postoperative feedback date. The computer platform is further operative to obtain preoperative patient data characterizing a spine of a defined-patient, generate a spinal surgery plan for the defined-patient based on processing the preoperative patient data through the machine learning model, and provide the spinal surgery plan to a display device for review by a user.

Elements of the computer platform which obtain the intraoperative feedback data and/or postoperative feedback data and which train the machine learning model may be the same as or different than elements of the computer platform which obtain the preoperative patient data, generate the spinal surgery plan, and provide the spinal surgery plan to the display device. The computer platform may include one or processors which execute software instructions in one or more memories and/or may include application specific integrated circuits. Multiple processors may be collocated and interconnected on a common substrate or common backplane or may be geographically distributed and communicatively connected through one or more local and/or wide-area communication networks.

Various embodiments disclosed herein are directed to improvements in operation of a surgical planning system providing navigated guidance when planning for and performing spinal surgical procedures, such as Interlaminar Lumbar Instrumented Fusion (ILIF) procedure, and spinal correction surgery which may include vertebral body replacement and/or disc replacement. A surgical planning system includes a machine learning model that can be adapted, trained, and configured to provide patient customized guidance during preoperative stage planning, intraoperative stage surgical procedures, and postoperative stage assessment. A database, e.g., centralized database, can store data that can be obtained in each of the stages across all patients who have previously used or are currently using the surgical planning system. In some embodiments, the machine learning model can be trained over time based on data from the database so that the patient customized guidance provides improved surgical outcomes.

Training of the machine learning model can include training based on learned correlations between patient data and surgical outcomes, correlations between cause and effect of various spine surgery elements including, for example, direct versus indirect spine decompression and amount (degree) of either, differences between spinal surgery techniques, actual amount of spinal correction achieved as a function of particular spinal surgery technique and surgical implants used, etc. Training of the machine learning model may be performed repetitively, e.g., continually when new data is obtained, in order to further improve surgical outcomes obtained by the spinal surgery plans generated from the machine learning model.

The machine learning model can use artificial intelligence techniques and may include a neural network model. The machine learning model may use centralized learning or federated learning techniques.

Figure 3:
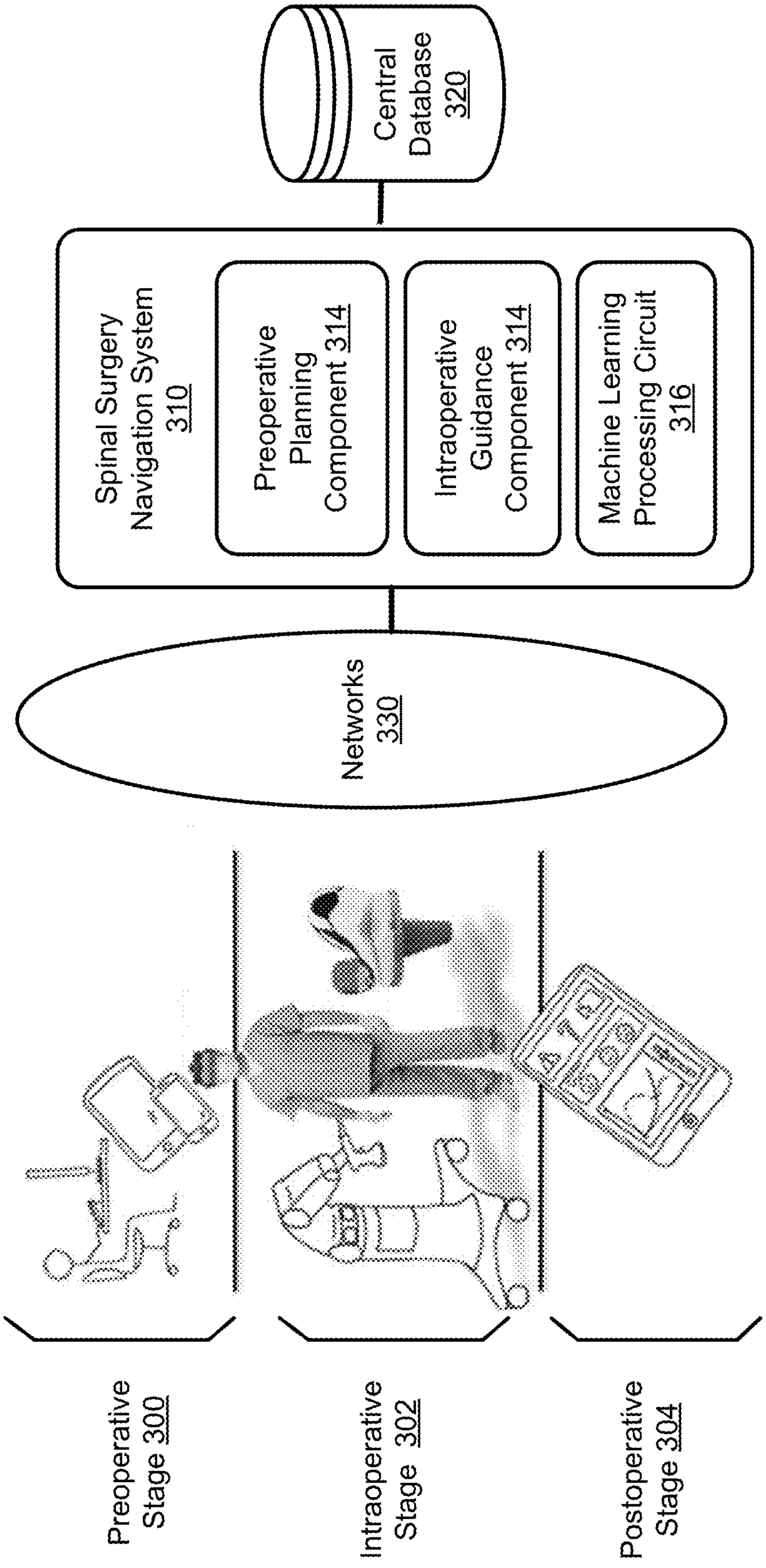
FIG. 3 illustrates a navigated spinal surgery workflow which uses a surgical planning system configured in accordance with some embodiments.

FIG. 3 illustrates a navigated spinal surgery workflow which uses a surgical planning system 310 configured in accordance with some embodiments. Referring to FIG. 3, three stages of workflow are illustrated: preoperative stage 300; intraoperative stage 302; and postoperative stage 304. During the preoperative stage 300, a user (e.g., surgeon) generates a surgical plan (case) based on analyzed patient images with assistance from the surgical planning system 310. During the intraoperative stage 302, the surgical planning system 310 uses a spinal surgery plan to provide navigated surgical assistance to the user, which may include displaying information and/or graphical indications to guide the user's actions, and/or provide instructions to guide a surgical robot for precise plan execution. During the postoperative stage 304, postoperative feedback data characterizing surgery outcomes is collected by the surgical planning system 310, such as by patient measurements and/or patient surveys, etc. Data obtained across all phases 300-304 can be stored in a central database 320 for use by the surgical planning system 310 to train a machine learning model of a machine learning processing circuit 316 (FIG. 4). The machine learning model can include artificial intelligence (AI) processes, neural network components, etc. The machine learning model can be initially trained and then further trained over time to generate more optimal spinal surgery plans customized for patients that result in improved surgical outcomes. Further example types of data that can be collected during the preoperative stage 300, intraoperative stage 302, and postoperative stage 304 are discussed further below with regard to, e.g., FIG. 5.

The example surgical planning system 310 shown in FIG. 3 includes a preoperative planning component 312, an intraoperative guidance component 314, a machine learning processing circuit 316, and a feedback training component 410.

As will be explained in further detail below regarding FIG. 4, a feedback training component 410 is configured to obtain postoperative feedback data which may be provided by distributed networked computers regarding surgical outcomes for a plurality of patients, and to train a machine learning model based on the postoperative feedback data. Although FIG. 3 shows a single computer, e.g., smart phone, providing postoperative feedback data during the postoperative stage 304 through one or more networks 330 (e.g., public (Internet) networks and or private networks) to the surgical planning system 310 for storage in the central database 320, it is to be understood that numerous network computers (e.g., hundreds of computers) could provide postoperative feedback data for each of many patients to the surgical planning system 310 (i.e., to the feedback training component 410) for use in training the machine learning model. Moreover, as explained in further detail below, the feedback training component 410 can further train the machine learning model based on preoperative data obtained during the preoperative stage 300 for numerous patients and based on intraoperative data obtained during the intraoperative stage 302 for numerous patients. For example, the training can include adapting rules of a machine learning (e.g., artificial intelligence) algorithm, rules of one or more sets of decision operations, and/or weights and/or firing thresholds of nodes of a neural network model, to drive one or more defined key performance surgical outcomes indicated by the preoperative data and/or the intraoperative data toward one or more defined thresholds or other rule(s) being satisfied.

The preoperative planning component 312 obtains preoperative data from one or more computers which characterizes a defined-patient, and generates a spinal surgery plan for the defined-patient based on processing the pre-operative data through the machine learning model. The pre-operative planning component 312 provides the spinal surgery plan to a display device for review by a user. Accordingly, the preoperative planning component 312 of the machine learning processing circuit 316 generates a spinal surgery plan for a defined-patient using the machine learning model which has been trained based on the postoperative feedback data regarding surgical outcomes for the plurality of patients. The training of the machine learning model can be repeated as more postoperative feedback is obtained by the feedback training component 410 so that the spinal surgery plans that are generated will become more continuous improved at providing more optimal surgical outcomes for patients.

Figure 4:
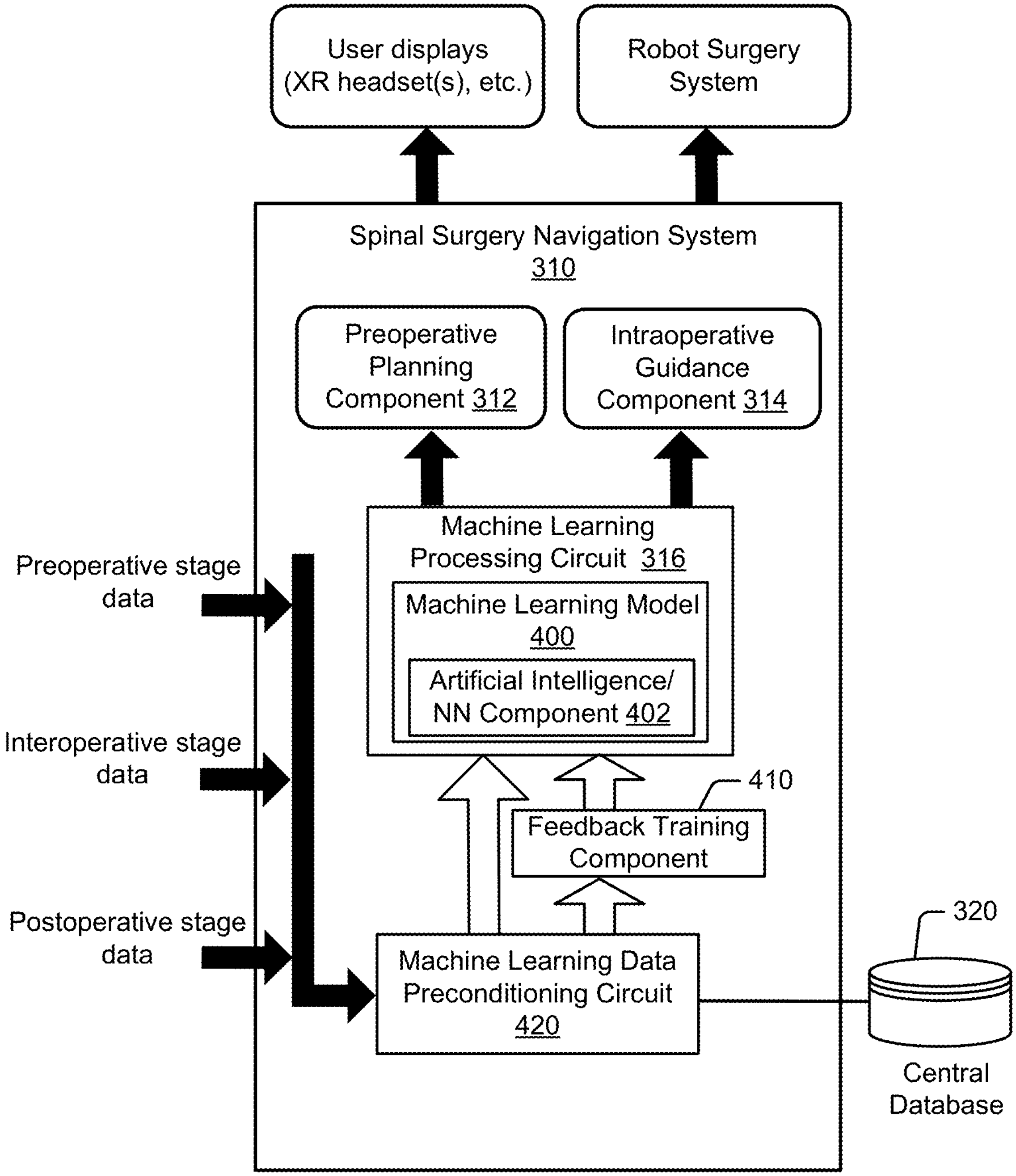
FIG. 4 illustrates a block diagram of the surgical planning system with associated data flows during the preoperative, intraoperative, and postoperative stages, and shows surgical guidance being provided to user displays and to a robot surgery system in accordance with some embodiments.

FIG. 4 illustrates a block diagram of the surgical planning system 310 with associated data flows during the preoperative, intraoperative, and postoperative stages, and shows surgical guidance being provided to user displays and to a robot surgery system, configured in accordance with some embodiments.

Referring to FIG. 4, the surgical planning system 310 includes the feedback training component 410, the preoperative planning component 312, and the intraoperative guidance component 314. The surgical planning system 310 also includes machine learning processing circuit 316 that includes the machine learning model 400, which may include an artificial intelligence and/or neural network component 402 as explained in further detail below.

The surgical planning system 310 contains a computing platform that is operative to obtain intraoperative feedback data and/or postoperative feedback data regarding spinal surgery outcome for a plurality of patients. A feedback training component 410 is operative to train the machine learning model 400 based on the intraoperative feedback data and/or the postoperative feedback data. The intraoperative feedback data and/or postoperative feedback data may also be stored in the central database 320.

Preoperative patient data characterizing a spine of a defined-patient is obtained and may be preconditioned by a machine learning data preconditioning circuit 420, e.g., weighted and/or filtered, before being processed through the machine learning model 400 to generate a spinal surgery plan for the defined-patient. The spinal surgery plan may be provided to a display device during preoperative planning. During surgery, the spinal surgery plan may be provided to XR headset(s) (also “head mounted display”) worn by a surgeon and other operating room personnel and/or provide to other display devices to provide real-time navigated guidance to personnel according to the spinal surgery plan. Alternatively or additionally, the spinal surgery plan can be converted into instructions that guide movement of a robot surgery system, as will be described in further detail below.

The operation of the surgical planning system 310 to generate the spinal surgery plan may include to process the preoperative patient data through the machine learning model to identify predicted improvements to key points captured in medical images of the spine of the defined-patient, to output data indicating a planned access trajectory to access a target location on the spine of the defined-patient and/or data indicating a planned approach trajectory for implanting an implant device at the target location on the spine of the defined-patient, and/or to output data indicating at least one of: a planned implant location on the spine of the defined-patient; a planned size of an implant to be implanted on the spine of the defined-patient; and a planned interbody implant expansion parameter.

The operation of the surgical planning system 310 to generate the spinal surgery plan may include to process the preoperative patient data through the machine learning model to output data indicating planned amount of spine decompression to be surgically performed and/or indicating a planned amount of disc material of the spine to be surgically removed by a discectomy procedure.

The operation of the surgical planning system 310 to generate the spinal surgery plan may include to process the preoperative patient data through the machine learning model to output data indicating a planned curvature shape for a rod to be implanted during spinal fusion.

In some further embodiments, the surgical planning system 310 can be further operative to obtain defined-patient intraoperative feedback data that includes at least one of: data characterizing deviation between an intraoperative spinal surgery process performed on the defined-patient and the spinal surgery plan for the defined-patient; data characterizing deviation between an intraoperative access trajectory used to access a target location on the spine of the defined-patient and an access trajectory indicated by the spinal surgery plan for the defined-patient; and data characterizing deviation between an intraoperative approach trajectory used to implant an implant device at the target location on the spine of the defined-patient and an approach trajectory indicated by the spinal surgery plan for the defined-patient. The feedback training component 410 can be configured to train the machine learning model 400 based on the defined-patient intraoperative feedback data.

In some further embodiments, the surgical planning system 310 can be further operative to obtain defined-patient intraoperative feedback data that includes at least one of: data characterizing an intraoperative measurement of amount of spine decompression obtained during spinal surgery according to the spinal surgery plan on the defined-patient; data characterizing an intraoperative measurement of amount of soft tissue disruption during spinal surgery according to the spinal surgery plan on the defined-patient; and data characterizing an intraoperative measurement of amount of disc material of the spine surgically removed by a discectomy procedure according to the spinal surgery plan on the defined-patient. The feedback training component 410 can be configured to train the machine learning model 400 based on the defined-patient intraoperative feedback data.

In some further embodiments, the surgical planning system 310 can be further operative to obtain defined-patient intraoperative feedback data that includes at least one of: data characterizing postoperative measurements of spine decompression captured in medical images of the spine of the defined-patient following spinal surgery; data characterizing postoperative measurements of spinal deformation captured in medical images of the spine of the defined-patient following spinal surgery; data characterizing postoperative measurements of amount of removed disc material of the spine captured in medical images of the spine of the defined-patient following the spinal surgery; and data characterizing postoperative measurements of amount of soft tissue disruption captured in medical images of the defined-patient following the spinal surgery. The feedback training component 410 can be configured to train the machine learning model 400 based on the defined-patient postoperative feedback data.

In some further embodiments, the surgical planning system 310 can be further operative to obtain defined-patient postoperative feedback data that includes at least one of: data characterizing implant failure following spinal surgery on the defined-patient; data characterizing bone failure following spinal surgery on the defined-patient; data characterizing bone fusion following spinal surgery on the defined-patient; and data characterizing patient reported outcome measures following spinal surgery on the defined-patient. The feedback training component 410 can be configured to train the machine learning model 400 based on the defined-patient postoperative feedback data.

The machine learning model 400 can include a neural network component 402 that includes an input layer having input nodes, a sequence of hidden layers each having a plurality of combining nodes, and an output layer having output nodes. At least one processing circuit (e.g., data preconditioning circuit 420) can be configured to provide different entries of the intraoperative feedback data and/or the postoperative feedback data to different ones of the input nodes of the neural network component 402, and to generate the spinal surgery plan based on output of output nodes of the neural network component 402.

The feedback training component 410 may be configured to adapt weights and/or firing thresholds that are used by the combining nodes of the neural network component 402 based on values of the intraoperative feedback data and/or the postoperative feedback data.

A machine learning data preconditioning circuit 420 may be provided that pre-processes the obtained data, such as by providing normalization and/or weighting of the various types of obtained data, which is then provided to machine learning processing circuit 316 during a run-time phase or to the feedback training component 410 during a training phase for use in training the machine learning model 400. In some embodiments, the training is performed continuously or at least occasionally during run-time.

A preoperative planning component 312 contains preoperative data from one of the distributed network computers characterizing a defined-patient, generates a spinal surgery plan for the defined-patient based on processing the preoperative data through the machine learning model 400, and provides the spinal surgery plan to a display device for review by a user.

Thus, as explained above, the training can include adapting rules of an AI algorithm, rules of one or more sets of decision operations, and/or weights and/or firing thresholds of nodes of a neural network mode, to drive one or more defined key performance surgical outcomes indicated by the preoperative data and/or the intraoperative data toward one or more defined thresholds or other rule(s) being satisfied.

The machine learning model 400 can be configured to process the preoperative data to output the spinal surgery plan identifying an implant device, a pose for implantation of the implant device in the defined-patient, and a predicted postoperative performance metric for the defined-patient following the implantation of the implant device.

Figure 8:
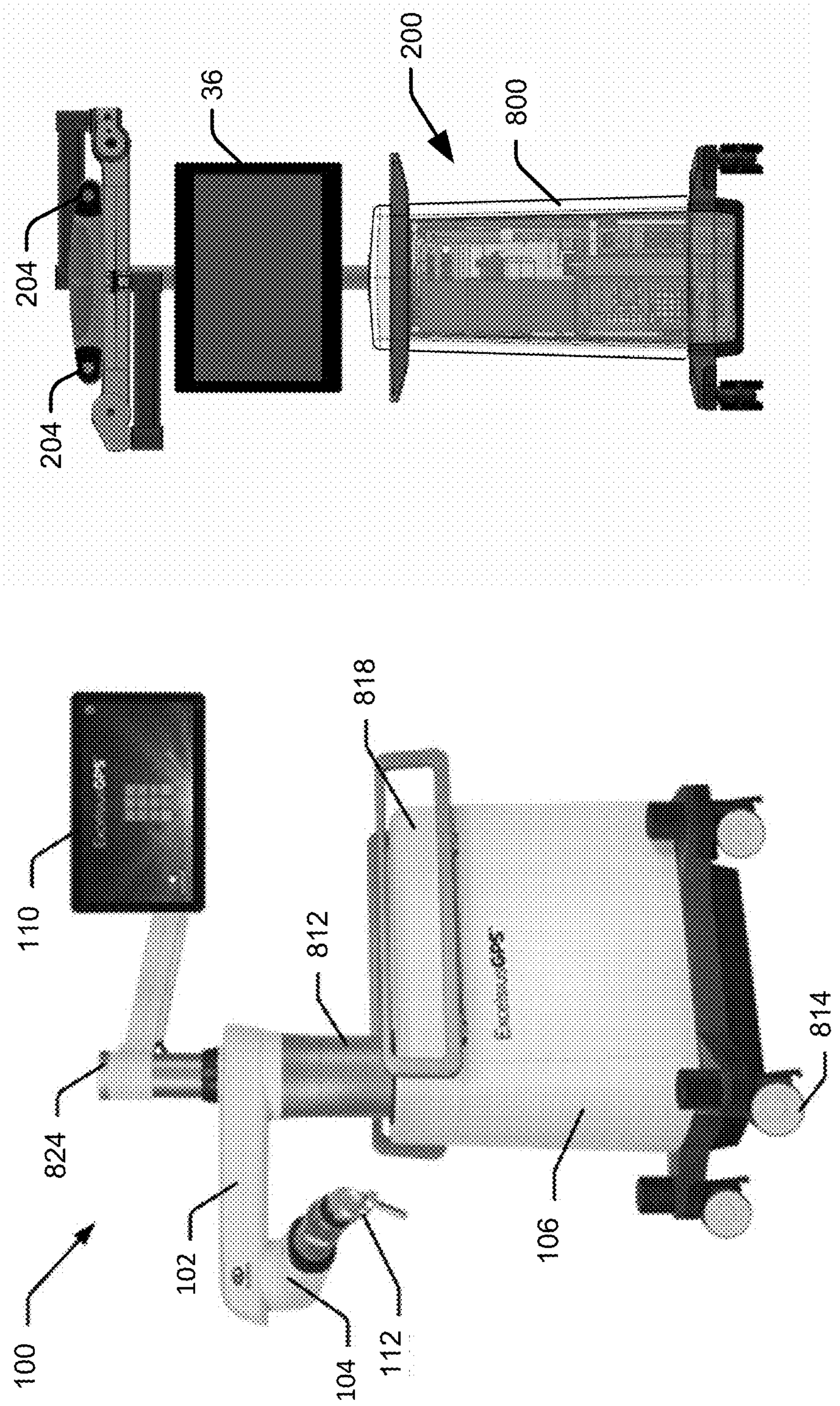
FIG. 8 further illustrates the camera tracking system and the surgical robot configured according to some embodiments.

The machine learning model 400 can be further configured to generate the spinal surgery plan with identification of planned access trajectory to access a target location on the spine of the defined-patient and/or data indicating a planned approach trajectory for implanting an implant device at the target location on the spine of the defined-patient. A preoperative planning component 312 may provide data of the spinal surgery plan to a computer platform 900 (e.g., FIG. 9) that allows review and modification of the plan by a surgeon. An intraoperative guidance component 314 may provide navigation information according to the spinal surgery plan to one or more display devices for viewing by a surgeon and/or other operating room personnel, e.g., to see-through display device 928 in an extended reality (XR) headset 140 (FIGS. 6 and 9) for viewing as an overlay on the defined-patient. The intraoperative guidance component 314 may provide steering information to a robot controller of a surgical robot 100 (FIGS. 6-8). The surgical robot 100 can include a robot base, a robot arm connected to the robot base and configured to guide movement of the surgical instrument, and at least one motor operatively connected to control movement of the robot arm relative to the robot base. The robot controller can control movement of the at least one motor based on the steering information to guide repositioning of the surgical instrument to become aligned with the target pose.

Figure 9:
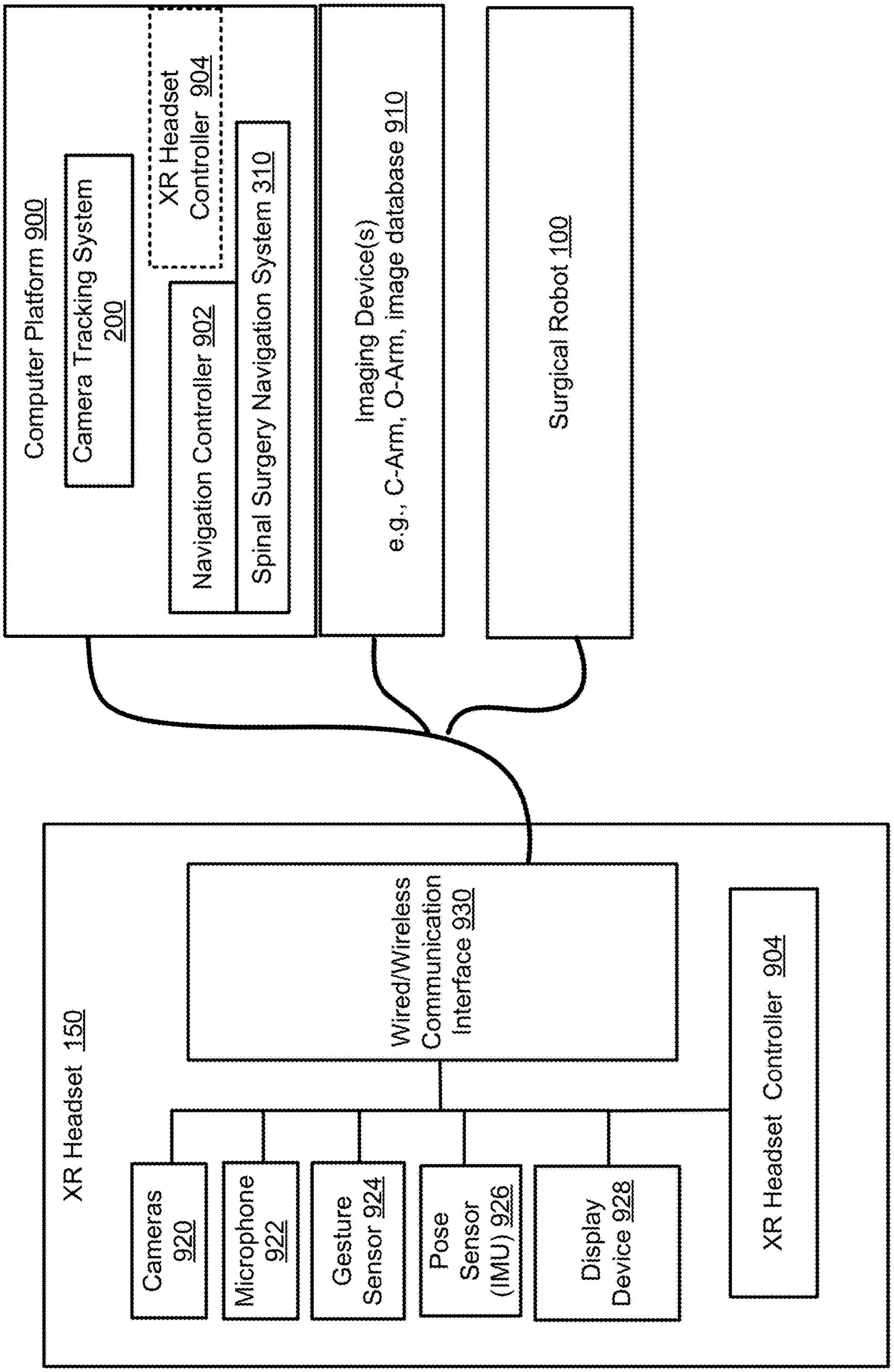
FIG. 9 illustrates a block diagram of a surgical system that includes an extended reality headset, a computer platform, imaging devices, and a surgical robot which are configured to operate according to some embodiments.

During surgery (i.e., the intraoperative stage) the surgical planning system 310 can be configured to provide the surgical plan to a display device to assist a user (e.g., surgeon) during surgery. In some embodiments, a surgical system includes the surgical planning system 310 as a subsystem for computer assisted navigation during surgery, a camera tracking subsystem 200 (FIGS. 6-8), and a navigation controller 902 (FIG. 9). As explained above, the surgical planning system 310 is configured to: obtain postoperative feedback data provided by distributed networked computers regarding surgical outcomes for a plurality of patients; train a machine learning model based on the postoperative feedback data; and obtain preoperative data from one of the distributed network computers characterizing a defined-patient, generate a spinal surgery plan for the defined-patient based on processing the preoperative data through the machine learning model.

The camera tracking subsystem 200 (FIGS. 6-8) is configured to determine the pose of the spine of the defined-patient relative to a pose of a surgical instrument manipulated by an operator and/or a surgical robot. The navigation controller 902 (FIG. 9) is operative to obtain the spinal surgery plan from the spinal surgery navigation subsystem 310, determine a target pose of the surgical instrument based on the spinal surgery plan indicating where a surgical procedure is to be performed on the spine of the defined-patient and based on the pose of the spine of the defined-patient, and generate steering information based on comparison of the target pose of the surgical instrument and the pose of the surgical instrument.

In some embodiments, the surgical system includes an XR headset 920 with at least one see-through display device 928 (FIG. 9). An XR headset controller 904 may partially reside in the computer platform 900 or in the XR headset 140, and is configured to generate a graphical representation of the steering information that is provided to the at least one see-through display device of the XR headset 920 to provide navigated guidance to the wearer according to the spinal surgery plan. For example, the navigation controller may be operative to generate a graphical representation of the steering information that is provided to XR headset controller 904 for display through the see-through display device 928 of the XR headset 140 to guide operator movement of the surgical instrument to become aligned with a target pose according to the spinal surgery plan.

To generate the spinal surgery plan and train the machine learning model 316, data is needed from multiple sources to establish a baseline machine learning model that is then trained over time to provide improved patent specific outcomes from the generated spinal surgery plans.

Figure 5:
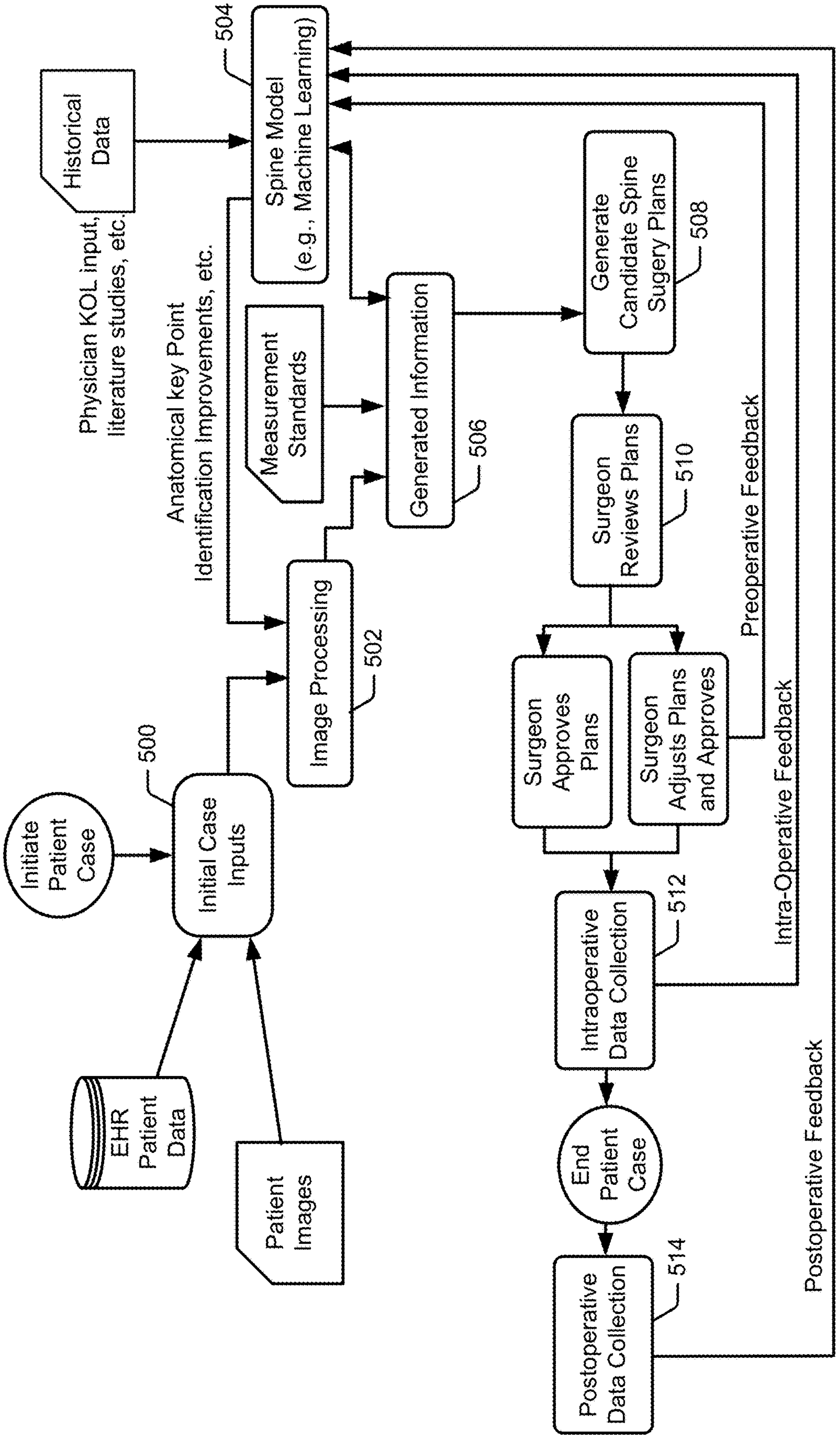
FIG. 5 illustrates an operational flowchart for generating a spinal surgery plan based on processing preoperative patient data through a spine model, and for using intraoperative feedback data and/or postoperative feedback data to adapt or machine-train the spine model in accordance with some embodiments.

FIG. 5 illustrates an operational flowchart for generating a spinal surgery plan based on processing preoperative patient data through a spine model 504, and for using intraoperative feedback data and/or postoperative feedback data to adapt or machine-train (via machine learning operations) the spine model 504.

Referring to FIG. 5, responsive to initiation of a patient case, preoperative data is provided as initial patient case inputs 500. The preoperative initial patient case input parameters 500 may be obtained from EHR patient data and/or patient images.

The electronic health record (EHR) patient data may include, without limitation, any one or more of:

1) date of birth, which may be used to select parameters for the spine model, e.g., adult or pediatric;
2) height;
3) weight/BMI;
4) gender;
5) ethnicity;
6) race;
7) bone Density, e.g., obtained from test results of Dual-Energy X-ray Absorptiometry (DEXA) scan (t-score and z-score), and/or CT scan (Hounsfield Scale);
8) menarchal status;
9) skeletal of maturity, e.g., Sander's score;
10) complete Blood Count (CBC);
11) blood Morphogenic Proteins (BMP);
12) coagulation Factors;
13) EKGs;
14) medication history, e.g., teriparatide status or other medications influencing bone density;
15) general medical history, e.g., nicotine status, substance abuse, medical conditions, known allergies, previous failed spinal surgeries, diabetes, rheumatoid arthritis, any degenerative diseases;
16) psychological evaluation section;
17) demographic characteristics;
18) activity characteristics-physical therapy status, activity level descriptor;
19) doctor's notes;
20) past spinal surgical procedures, e.g., fusions, spinal cord stimulator, non-surgical interventions, etc.;
21) current diagnoses, e.g., pathologies/location; radiculopathy, myelopathy; and
22) patient imaging scans.

Historical data can be provided to the spine model 504 for adaptation/training of the model 504 and for use in generating machine learning-based outputs that may be used to perform the image processing 502 and/or to determine the generated information 506 and generate the candidate spine surgery plans 508. The historical data may include, without limitation, physician Key Opinion Leader (KOL) data input and/or data from literature studies such as any one or more of:

1) spinal anatomical trends, e.g., size, shape, patterns;
2) spinal alignment parameters, e.g., accepted normative ranges;
3) spinal alignment measurement methodologies;
4) spinal stiffness matrix;
5) initial trained machine learning algorithms from preop and/or postop patient images with known outcomes;
6) surgical intervention expertise; and
7) diagnosis criteria(s).

More specifically in the context of spinal surgery, the historical data may include any one or more of: spinal alignment target values; spinal anatomical trends; surgeon approach techniques; spine stiffness data; diagnosis criteria; and known correlations for best outcomes from surgical techniques.

The patient images may be obtained from imaging devices 910 (FIG. 9), such as a computed tomography C-arm image device and/or computed tomography O-arm imaging device, and/or may be obtained from image database(s). The patient images may be retrieved from the central database 320 (FIG. 3) using a patient identifier.

Image processing 502 of the patient images may be performed using the spine model 504 which can be configured to generate synthetic CT image modality images of the patient's spine from MRI modality images of the patient's spine. Other image processing 502 operations can include generating synthetic CT image modality images from a plurality of fluoroscopy shots, e.g., AP and lateral fluoroscopy images.

Alternatively or additionally, the image processing may be performed using the spine model 504 which can be configured to identify anatomical key points and datums, determine segmentation, colorization, and/or identify patient spinal anatomy, e.g., bone and soft tissue structures. Sizes of the images anatomical structures can be determined based on segment locations and overall structure size. Spine stiffness and bone density may be estimated based on the image processing and the other initial case inputs. Stenosis of the spine, central and/or lateral recess, can be characterized based on processing initial case inputs 500 through the spine model 504. Foraminal height(s), disc height(s) (e.g., anterior or posterior, medial or lateral), CSF fluid around spinal cord and nerve roots, current global alignment parameters, can be characterized based on processing initial case inputs 500 through the spine model 504 and using measurement standards.

Generated information 506 from the initial case inputs 500, image processing 502, and measurement standards, and historical data, along with output of the spine model 504, can include, but is not limited to, any one or more of the following:

1) medical diagnoses of the patient, such as inputs from surgeon and/or output from the spine model 504;
2) one or more candidate spine surgery plans;
3) predication of likelihood of complications from surgery performed according to the one or more candidate spine surgery plans, which may be based on inputs from surgeon and/or output from the spine model 504;

4) predicted ideal global alignment parameters and level of intervention needed;
5) approach options with predicted outcomes displayed as function of:
   i. direct versus indirect, e.g., when is indirect decompression a sufficient intervention;
   ii. indirect decompression options and/or scenarios;
   iii. implant auto-plans, e.g., interbody size, location, lordosis or expansion parameters, fixation implant size and/or location, rod size and/or diameter and/or material, collision avoidance, instrument depth control set points;
   iv. deformity solution(s);
   v. auto-plan of rod curvature to align with posterior instrumentation and ability to translate that plan to an automatic rod bender instrument;
   vi. foraminal and/or spinal canal height restoration prediction; and
   vii. alignment correction.

The surgeon reviews 510 the one or more candidate spine surgery plans and may approve (select) one of the candidate spine surgery plans or adjust one of the candidate spine surgery plans for approval. The approved candidate spine surgery plan is provided as preoperative feedback to train the spine model 504.

The approved candidate spine surgery plan can be provided to the intraoperative guidance component 314 (FIG. 3) where it can be used to generate navigation information to guide an surgeon or other personnel through a spinal surgery procedure according to the approved candidate spine surgery plan. Alternatively or additionally, the intraoperative guidance component 314 may provide the approved candidate spine surgery plan as steering information to the robot controller to control movement of the robot arm according to the approved candidate spine surgery plan.

Intraoperative data is collected 512 and is provided as intraoperative feedback for training the spine model 504. The Intraoperative data can include, but is not limited to, any one or more of the following:

1) finalized implant plans, e.g., spine level, type (VBR, disc replacement, interbody spacer), size, expansion parameters, location data in reference to anatomical key points and implant position;
2) finalized access approach, e.g., anterior cervical discectomy and fusion (ACDF), Posterior Cervical, lateral lumbar interbody fusion (LLIF), anterior lumbar interbody fusion (ALIF), posterior lumbar interbody fusion (PLIF), transforaminal lumbar interbody fusion (TLIF), etc.;
3) Port sizes used, such as biportal or uniportal sizes;
4) intraoperative vertebral body and instrumentation navigation and location history tracking, which may include any one or more of:
   i. comparison of tracked vertebral body alignment measures;
   ii. degree of soft tissue disruption, e.g., based on approach, access style, level of decompression;
   iii. degree of direct decompression or resection;
   iv. port size used, which may include total working region versus actual bone removed within a working region;
   v. implant cannula placement;
   vi. degree of discectomy tissue removed;
   vii. force measurements, e.g., from corrective loads, implant loads; and
   viii. stiffness sensors;
5) smart driver information feedback on torque and expansion;
6) smart implant information feedback on load and/or force distributions across implant, position;
7) neuromonitoring data;
8) ultrasonics data;
9) biologics used;
10) robot surgery system operation data logs;
11) surgical time, e.g., access, decompressions, discectomy, interbody placement, fixation placement, overall, etc;
12) re-registration scans; and
13) updates to measured parameters and/or plan based on new registration.

After the patient surgical procedure has been completed (end patient case), postoperative data is collected 514 and is provided as postoperative feedback for training the spine model 504. The postoperative data can include, but is not limited to, any one or more of the following:

1) Patient Reported Outcomes (PROs);
2) postoperative patient imaging scans;
3) deviation of spinal surgery plan versus actual placement of implants, which may be determined through preoperative patient imaging scans with implant plans compared to postoperative patient imaging scans;
4) expected lordosis and/or correction compared to actual, e.g., which can be used to establish expected accuracies and outcomes and which indicate height restoration such as disc height, foraminal height (left vs. right), etc.;
5) implant failures;
6) bone failures;
7) fusion rates;
8) ASD reporting (levels affected in relation to surgical intervention, evidence of facet violation (if any));
9) Patient Reported Outcome Measures (PROMs); and
10) short-term and long-term patient medical data measurements, and observed changes over time in the data measurements.

Through machine learning, anatomical standards, pre/intra/post-operative data collection, and known patient outcomes), the spine model 504 can be trained and eventually be predictive enough to determine or suggest possible diagnoses, determine ideal access approach(es), degree of decompression needed (indirect and/or direct), required interbody size/placement, custom interbody expansion set points (height and lordosis), and fixation type/size/placement that would be required for the most ideal spinal correction and patient outcomes. The need for this type of capability ranges from complex spinal deformity cases to single level degenerative spinal cases, like in the ILIF procedure, and could be beneficial for every type of spinal correction surgery including vertebral body replacements, and disc replacements.

Improvement of preoperative spinal surgery plans can be provided by analysis of intraoperative and postoperative data. Use of the preoperative feedback, intraoperative feedback, and postoperative feedback to train the spine model 504 can enable more accurate prediction of patient specific outcomes through a candidate spine surgery plan and the generation of the spine surgery plan can be optimized to provide more optimal patient specific outcomes. The spine surgery plan generated using the trained spine model 504 can use more optimally selected procedure types, implant types, access types, levels (amount) of decompression needed (indirect versus direct, and amount (degrees) of either), etc. The operations can be performed using x-ray imaging, endoscopic camera imaging, and/or ultrasonic imaging. The spinal surgery plan(s) can be generated based on learned surgeon preference(s) and/or learned standard best practices.

Various embodiments of the present disclosure may use postoperatively obtained data for correlation with a surgical plan and execution in order to:

- Provide guidance information that enables a user to understand performance metrics that are predicted to be obtained through the selection of available surgical plan variables; and
- Provide machine learning, such may include artificial intelligence (AI), assistance to a surgeon when performing patient-specific planning:
  - Defining target deformity correction(s) and/or joint line(s) through the planned surgical procedure; and/or
  - Defining selection of a best implant for use with the patient.

FIG. 6 is an overhead view of a surgical system arranged during a surgical procedure in a surgical room. The system includes a camera tracking system 200 for computer assisted navigation during surgery and may further include a surgical robot 100 for robotic assistance according to some embodiments. FIG. 7 illustrates the camera tracking system 200 and the surgical robot 100 positioned relative to a patient according to some embodiments. FIG. 8 further illustrates the camera tracking system 200 and the surgical robot 100 configured according to some embodiments. FIG. 9 illustrates a block diagram of a surgical system that includes headsets 140 (e.g., extended reality (XR) headsets), a computer platform 900, imaging devices 910, and the surgical robot 100 which are configured to operate according to some embodiments.

The XR headsets 140 may be configured to augment a real-world scene with computer generated XR images while worn by personnel in the operating room. The XR headsets 140 may be configured to provide an augmented reality (AR) viewing environment by displaying the computer generated XR images on a see-through display screen that allows light from the real-world scene to pass therethrough for combined viewing by the user. Alternatively, the XR headsets 140 may be configured to provide a virtual reality (VR) viewing environment by preventing or substantially preventing light from the real-world scene from being directly viewed by the user while the user is viewing the computer-generated AR images on a display screen. The XR headsets 140 can be configured to provide both AR and VR viewing environments. Thus, the term XR headset can be referred to as an AR headset or a VR headset.

Referring to FIGS. 6 through 9, the surgical robot 100 may include one or more robot arms 104, a display 110, an end-effector 112 (e.g., a guide tube 114), and an end effector reference element which can include one or more tracking fiducials. A patient reference element 116 (DRB) has a plurality of tracking fiducials and is secured directly to the patient 210 (e.g., to a bone of the patient). A reference element 144 is attached or formed on an instrument, surgical tool, surgical implant device, etc.

The camera tracking system 200 includes tracking cameras 204 which may be spaced apart stereo cameras configured with partially overlapping field-of-views. The camera tracking system 200 can have any suitable configuration of arm(s) 202 to move, orient, and support the tracking cameras 204 in a desired location, and may contain at least one processor operable to track location of an individual fiducial and pose of an array of fiducials of a reference element.

As used herein, the term "pose" refers to the location (e.g., along 3 orthogonal axes) and/or the rotation angle (e.g., about the 3 orthogonal axes) of fiducials (e.g., DRB) relative to another fiducial (e.g., surveillance fiducial) and/or to a defined coordinate system (e.g., camera coordinate system, navigation coordinate system, etc.). A pose may therefore be defined based on only the multidimensional location of the fiducials relative to another fiducial and/or relative to the defined coordinate system, based on only the multidimensional rotational angles of the fiducials relative to the other fiducial and/or to the defined coordinate system, or based on a combination of the multidimensional location and the multidimensional rotational angles. The term "pose" therefore is used to refer to location, rotational angle, or combination thereof.

The tracking cameras 204 may include, e.g., infrared cameras (e.g., bifocal or stereophotogrammetric cameras), operable to identify, for example, active and passive tracking fiducials for single fiducials (e.g., surveillance fiducial) and reference elements which can be formed on or attached to the patient 210 (e.g., patient reference element, DRB, etc.), end effector 112 (e.g., end effector reference element), XR headset(s) 140 worn by a surgeon 120 and/or a surgical assistant 126, etc. in a given measurement volume of a camera coordinate system while viewable from the perspective of the tracking cameras 204. The tracking cameras 204 may scan the given measurement volume and detect light that is emitted or reflected from the fiducials in order to identify and determine locations of individual fiducials and poses of the reference elements in three-dimensions. For example, active reference elements may include infrared-emitting fiducials that are activated by an electrical signal (e.g., infrared light emitting diodes (LEDs)), and passive reference elements may include retro-reflective fiducials that reflect infrared light (e.g., they reflect incoming IR radiation into the direction of the incoming light), for example, emitted by illuminators on the tracking cameras 204 or other suitable device.

The XR headsets 140 may each include tracking cameras (e.g., spaced apart stereo cameras) that can track location of a surveillance fiducial and poses of reference elements within the XR camera headset field-of-views (FOVs) 141 and 142, respectively. Accordingly, as illustrated in FIG. 6, the location of the surveillance fiducial and the poses of reference elements on various objects can be tracked while in the FOVs 141 and 142 of the XR headsets 140 and/or a FOV 600 of the tracking cameras 204.

FIGS. 6 and 7 illustrate a potential configuration for the placement of the camera tracking system 200 and the surgical robot 100 in an operating room environment. Computer assisted navigated surgery can be provided by the camera tracking system controlling the XR headsets 140 and/or other displays 34, 36, and 110 to display surgical procedure navigation information. The surgical robot 100 is optional during computer assisted navigated surgery.

The camera tracking system 200 may operate using tracking information and other information provided by multiple XR headsets 140 such as inertial tracking information and optical tracking information (frames of tracking data). The XR headsets 140 operate to display visual information and may play-out audio information to the wearer. This information can be from local sources (e.g., the surgical robot 100 and/or other medical), imaging devices 910 (FIG. 11), and remote sources (e.g., patient medical image database), and/or other electronic equipment. The camera tracking system 200 may track fiducials in 6 degrees-of-freedom (6 DOF) relative to three axes of a 3D coordinate system and rotational angles about each axis. The XR headsets 140 may also operate to track hand poses and gestures to enable gesture-based interactions with "virtual" buttons and interfaces displayed through the XR headsets 140 and can also interpret hand or finger pointing or gesturing as various defined commands. Additionally, the XR headsets 140 may have a 1-10× magnification digital color camera sensor called a digital loupe. In some embodiments, one or more of the XR headsets 140 are minimalistic XR headsets that display local or remote information but include fewer sensors and are therefore more lightweight.

An "outside-in" machine vision navigation bar supports the tracking cameras 204 and may include a color camera. The machine vision navigation bar generally has a more stable view of the environment because it does not move as often or as quickly as the XR headsets 140 while positioned on wearers' heads. The patient reference element 116 (DRB) is generally rigidly attached to the patient with stable pitch and roll relative to gravity. This local rigid patient reference 116 can serve as a common reference for reference frames relative to other tracked elements, such as a reference element on the end effector 112, instrument reference element 144, and reference elements on the XR headsets 140.

When present, the surgical robot (also "robot") may be positioned near or next to patient 210. The robot 100 can be positioned at any suitable location near the patient 210 depending on the area of the patient 210 undergoing the surgical procedure. The camera tracking system 200 may be separate from the robot system 100 and positioned at the foot of patient 210. This location allows the tracking camera 200 to have a direct visual line of sight to the surgical area 208. In the configuration shown, the surgeon 120 may be positioned across from the robot 100, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. An anesthesiologist 122, nurse or scrub tech can operate equipment which may be connected to display information from the camera tracking system 200 on a display 34.

With respect to the other components of the robot 100, the display 110 can be attached to the surgical robot 100 or in a remote location. End-effector 112 may be coupled to the robot arm 104 and controlled by at least one motor. In some embodiments, end-effector 112 includes a guide tube 114, which is configured to receive and orient a surgical instrument, tool, or implant used to perform a surgical procedure on the patient 210. In some other embodiments, the end-effector 112 includes a passive structure guiding a saw blade (e.g., sagittal saw) along a defined cutting plate.

As used herein, the term "end-effector" is used interchangeably with the terms "end-effectuator" and "effectuator element." The term "instrument" is used in a non-limiting manner and can be used interchangeably with "tool" and "implant" to generally refer to any type of device that can be used during a surgical procedure in accordance with embodiments disclosed herein. The more general term device can also refer to structure of the end-effector, etc. Example instruments, tools, and implants include, without limitation, drills, screwdrivers, saws, dilators, retractors, probes, implant inserters, and implant devices such as a screws, spacers, interbody fusion devices, plates, rods, etc. Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument in a desired manner.

The surgical robot 100 is operable to control the translation and orientation of the end-effector 112. The robot 100 may move the end-effector 112 under computer control along x-, y-, and z-axes, for example. The end-effector 112 can be configured for selective rotation about one or more of the x-, y-, and z-axis, and a Z Frame axis, such that one or more of the Euler Angles (e.g., roll, pitch, and/or yaw) associated with end-effector 112 can be selectively computer controlled. In some embodiments, selective control of the translation and orientation of end-effector 112 can permit performance of medical procedures with significantly improved accuracy compared to conventional robots that utilize, for example, a 6 DOF robot arm comprising only rotational axes. For example, the surgical robot 100 may be used to operate on patient 210, and robot arm 104 can be positioned above the body of patient 210, with end-effector 112 selectively angled relative to the z-axis toward the body of patient 210.

In some example embodiments, the XR headsets 140 can be controlled to dynamically display an updated graphical indication of the pose of the surgical instrument so that the user can be aware of the pose of the surgical instrument at all times during the procedure.

In some further embodiments, surgical robot 100 can be operable to correct the path of a surgical instrument guided by the robot arm 104 if the surgical instrument strays from the selected, preplanned trajectory. The surgical robot 100 can be operable to permit stoppage, modification, and/or manual control of the movement of end-effector 112 and/or the surgical instrument. Thus, in use, a surgeon or other user can use the surgical robot 100 as part of computer assisted navigated surgery, and has the option to stop, modify, or manually control the autonomous or semi-autonomous movement of the end-effector 112 and/or the surgical instrument.

Fiducials of reference elements can be formed on or connected to robot arms 102 and/or 104, the end-effector 112 (e.g., end-effector element 114 in FIG. 9), and/or a surgical instrument (e.g., instrument element 144) to enable tracking of poses in a defined coordinate system, e.g., such as in 6 DOF along 3 orthogonal axes and rotation about the axes. The reference elements enable each of the marked objects (e.g., the end-effector 112, the patient 210, and the surgical instruments) to be tracked by the tracking camera 200, and the tracked poses can be used to provide navigated guidance during a surgical procedure and/or used to control movement of the surgical robot 100 for guiding the end-effector 112 and/or an instrument manipulated by the end-effector 112.

Referring to FIG. 10 the surgical robot 100 may include a display 110, upper arm 102, lower arm 104, end-effector 112, vertical column 812, casters 814, a handles 818, and ring 824 which uses lights to indicate statuses and other information. Cabinet 106 may house electrical components of surgical robot 100 including, but not limited to, a battery, a power distribution module, a platform interface board module, and a computer. The camera tracking system 200 may include a display 36, tracking cameras 204, arm(s) 202, a computer housed in cabinet 800, and other components.

In computer assisted navigated surgeries, perpendicular 2D scan slices, such as axial, sagittal, and/or coronal views, of patient anatomical structure are displayed to enable user visualization of the patient's anatomy alongside the relative poses of surgical instruments. An XR headset or other display can be controlled to display one or more 2D scan slices of patient anatomy along with a 3D graphical model of anatomy. The 3D graphical model may be generated from a 3D scan of the patient, e.g., by a CT scan device, and/or may be generated based on a baseline model of anatomy which isn't necessarily formed from a scan of the patient.

Example Surgical System

FIG. 9 illustrates a block diagram of a surgical system that includes an XR headset 140, a computer platform 900, imaging devices 910, and a surgical robot 100 which are configured to operate according to some embodiments. The computer platform 900 may include the surgical planning system 310 containing the computer platform configured to operate according to one or more of the embodiments disclosed herein.

The imaging devices 910 may include a C-arm imaging device, an O-arm imaging device, and/or a patient image database. The XR headset 140 provides an improved human interface for performing navigated surgical procedures. The XR headset 140 can be configured to provide functionalities, e.g., via the computer platform 900, that include without limitation any one or more of: identification of hand gesture-based commands, display XR graphical objects on a display device 928 of the XR headset 140 and/or another display device. The display device 928 may include a video projector, flat panel display, etc. The user may view the XR graphical objects as an overlay anchored to particular real-world objects viewed through a see-through display screen. The XR headset 140 may additionally or alternatively be configured to display on the display device 928 video streams from cameras mounted to one or more XR headsets 140 and other cameras.

Electrical components of the XR headset 140 can include a plurality of cameras 920, a microphone 922, a gesture sensor 924, a pose sensor 926 (e.g., inertial measurement unit (IMU)), the display device 928, and a wireless/wired communication interface 930. The cameras 920 of the XR headset 140 may be visible light capturing cameras, near infrared capturing cameras, or a combination of both.

The cameras 920 may be configured to operate as the gesture sensor 924 by tracking for identification user hand gestures performed within the field-of-view of the camera(s) 920. Alternatively, the gesture sensor 924 may be a proximity sensor and/or a touch sensor that senses hand gestures performed proximately to the gesture sensor 924 and/or senses physical contact, e.g., tapping on the sensor 924 or its enclosure. The pose sensor 926, e.g., IMU, may include a multi-axis accelerometer, a tilt sensor, and/or another sensor that can sense rotation and/or acceleration of the XR headset 140 along one or more defined coordinate axes. Some or all of these electrical components may be contained in a head-worn component enclosure or may be contained in another enclosure configured to be worn elsewhere, such as on the hip or shoulder.

As explained above, a surgical system includes the camera tracking system 200 which may be connected to a computer platform 900 for operational processing and which may provide other operational functionality including a navigation controller 902 and/or of an XR headset controller 904. The surgical system may include the surgical robot 100. The navigation controller 902 can be configured to provide visual navigation guidance to an operator for moving and positioning a surgical tool relative to patient anatomical structure based on a surgical plan, e.g., from a surgical planning function, defining where a surgical procedure is to be performed using the surgical tool on the anatomical structure and based on a pose of the anatomical structure determined by the camera tracking system 200. The navigation controller 902 may be further configured to generate navigation information based on a target pose for a surgical tool, a pose of the anatomical structure, and a pose of the surgical tool and/or an end effector of the surgical robot 100. The navigation information may be displayed through the display device 928 of the XR headset 140 and/or another display device to indicate where the surgical tool and/or the end effector of the surgical robot 100 should be moved to perform a surgical procedure according to a defined surgical plan.

The electrical components of the XR headset 140 can be operatively connected to the electrical components of the computer platform 900 through the wired/wireless interface 930. The electrical components of the XR headset 140 may be operatively connected, e.g., through the computer platform 900 or directly connected, to various imaging devices 910, e.g., the C-arm imaging device, the I/O-arm imaging device, the patient image database, and/or to other medical equipment through the wired/wireless interface 930.

The surgical system may include a XR headset controller 904 that may at least partially reside in the XR headset 140, the computer platform 900, and/or in another system component connected via wired cables and/or wireless communication links. Various functionality is provided by software executed by the XR headset controller 904. The XR headset controller 904 is configured to receive information from the camera tracking system 200 and the navigation controller 902, and to generate an XR image based on the information for display on the display device 928.

The XR headset controller 904 can be configured to operationally process frames of tracking data from tracking cameras from the cameras 920 (tracking cameras), signals from the microphone 1620, and/or information from the pose sensor 926 and the gesture sensor 924, to generate information for display as XR images on the display device 928 and/or for display on other display devices for user viewing. Thus, the XR headset controller 904 illustrated as a circuit block within the XR headset 140 is to be understood as being operationally connected to other illustrated components of the XR headset 140 but not necessarily residing within a common housing or being otherwise transportable by the user. For example, the XR headset controller 904 may reside within the computer platform 900 which, in turn, may reside within the cabinet 800 of the camera tracking system 200, the cabinet 106 of the surgical robot 100, etc.

Further Definitions and Embodiments

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being “connected”, “coupled”, “responsive”, or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, micro-code, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts is to be determined by the broadest permissible interpretation of the present disclosure including the following examples of embodiments and their equivalents, and shall not be restricted or limited by the foregoing detailed description.

What is claimed is:

1. A surgical planning system to provide computer assisted navigation for spinal surgery, the surgical planning system comprises a computer platform operative to:

obtain images of at least two different postures of a patient's spine;

measure displacement of anatomical features of the patient's spine between the images of the at least two different postures of the patient's spine;

estimate stiffness of the patient's spine based on the measurements of displacement;

generate a patient-specific kinematic model of the patient's spine based on the estimated stiffness; and provide a surgical plan based on the patient-specific kinematic model of the patient's spine.

2. The surgical planning system of claim 1, wherein the measurement of displacement of anatomical features of the patient's spine between the images of the at least two different postures of the patient's spine, comprises to:

measure the displacement of anatomical features of the patient's spine between images obtained by at least two different imaging modalities among a group of: computerized tomography (CT) imaging; magnetic resonance imaging (MRI); Cone Beam Computerized Tomography (CBCT) imaging; Micro Computerized Tomography (MCT) imaging; 3D ultrasound imaging, x-ray imaging, and fluoroscopy imaging.

3. The surgical planning system of claim 1, wherein the measurement of displacement of anatomical features of the patient's spine between the images of the at least two different postures of the patient's spine, comprises to:

measure the displacement of anatomical features of the patient's spine between at least two different ones of: a supine posture image of the patient's spine; a prone posture image of the patient's spine; a lateral posture image of the patient's spine, a standing posture image of the patient's spine; and a bending posture image of the patient's spine.

4. The surgical planning system of claim 3, wherein the measurement of displacement of anatomical features of the patient's spine between the images of the at least two different postures of the patient's spine, comprises to:

measure the displacement of anatomical features of the patient's spine between a first image and a second image, wherein the first image is based on a preoperative computerized tomography (CT) image or a preoperative magnetic resonance imaging (MRI) image of the patient's spine in one of a supine posture and a prone posture, wherein the second image is based on an intraoperative CT image or an intraoperative fluoroscopy image of the patient's spine in the other one of the supine posture and the prone posture.

5. The surgical planning system of claim 1, wherein the measurement of displacement of anatomical features of the patient's spine between the images of the at least two different postures of the patient's spine, comprises to:

measure the displacement of vertebral body centers and intervertebral disc centers of the patient's spine between the images of the at least two different postures of the patient's spine.

6. The surgical planning system of claim 1, wherein the computer platform is further operative to:

provide computer assisted navigation data based on the surgical plan to a display device for preoperative surgery planning and/or intraoperative assisted surgery navigation on the patient's spine, and/or provide computer assisted navigation data based on the surgical plan to a surgical robot to control movement of an end-effector of the surgical robot for computer assisted navigation during surgery on the patient's spine.

7. The surgical planning system of claim 1, wherein to estimate stiffness of the patient's spine based on the measurements of displacement, the computer platform is further operative to:

determine flexibility of intervertebral joints of the patient's spine based on the measurements of displacement of the intervertebral joints of the patient's spine between the images of the at least two different postures of the patient's spine;

obtain baseline biomechanical stiffness parameters of corresponding intervertebral joints of a baseline spine defined by a baseline spine model; and estimate the stiffness of the intervertebral joints of the patient's spine based on correlating the determined flexibility of the intervertebral joints of the patient's spine to the baseline biomechanical stiffness parameters of the corresponding intervertebral joints of the baseline spine defined by the baseline spine model.

8. The surgical planning system of claim 7, wherein to generate the patient-specific kinematic model of the patient's spine based on the estimated stiffness, the computer platform is further operative to:

generate a 3D model of the patient's spine based on registering the anatomical features of the patient's spine imaged in at least one of the images to corresponding anatomical features of the baseline spine defined by the baseline spine model; and generate the patient-specific kinematic model of the patient's spine using the estimate of the stiffness of the intervertebral joints of the patient's spine to operationally define relationships between levels of force applied to anatomical features of the 3D model of the patient's spine to resulting displacement of the anatomical features.

9. The surgical planning system of claim 8, wherein to generate the surgical plan based on the patient-specific kinematic model of the patient's spine, the computer platform is further operative to:

obtain a target displacement of at least one anatomical feature of the patient's spine;

estimate using the patient-specific kinematic model a level of force to be applied to at least one location on the patient's spine to obtain the target displacement of the at least one anatomical feature of the patient's spine.

10. The surgical planning system of claim 8, wherein to generate the surgical plan based on the patient-specific kinematic model, the computer platform is further operative to:

obtain a targeted displacement of anatomical features of the patient's spine through fixation of an implant to the patient's spine; and estimate using the patient-specific kinematic model a level of force that will be exerted on a surgical implant when used to fixate anatomical features of the patient's spine at the target displacement.

11. The surgical planning system of claim 10, wherein to estimate using the patient-specific kinematic model the level of force will be exerted on the surgical implant when used to fixate anatomical features of the patient's spine at the target displacement, the computer platform is further operative to:

estimate a level of force exerted on a pedicle screw to secure a spine fixation implant to fixate anatomical features of the patient's spine at the target displacement.

12. The surgical planning system of claim 1, wherein to generate the patient-specific kinematic model of the patient's spine based on the estimated stiffness, comprises to:

process the images of the at least two different postures of the patient's spine through a machine learning model to generate a function relating inputted levels of force to be applied to anatomical features of the patient's spine to outputted resulting displacement of the anatomical features, wherein the machine learning model is trained to relate displacement of intervertebral joints of spines between the images of the at least two different postures of the patient's spine to stiffness of the intervertebral joints of the patient's spine.

13. The surgical planning system of claim 1, further comprising wherein the computer platform is further operative to:

determine a target displacement of at least one anatomical feature of the patient's spine based on the surgical plan;

obtain tool tracking data indicating pose of a tool relative to the patient's spine;

obtain spine tracking data indicating pose of the at least one anatomical feature of the patient's spine;

process the tool tracking data, the spine tracking data, and the target displacement of the at least one anatomical feature of the patient's spine to generate intraoperative navigated guidance data; and display the intraoperative navigated guidance data to guide a user's movement of the tool.

14. The surgical planning system of claim 1, further comprising:

the surgical robot including a robot base, a robot arm connected between the robot base and an end effector, and at least one motor operatively connected to control movement of the end effector via the robot arm relative to the robot base, wherein the computer platform is further operative to determine a target displacement of at least one anatomical feature of the patient's spine based on the surgical plan;

obtain tool tracking data indicating pose of a tool relative to the patient's spine;

obtain spine tracking data indicating pose of the at least one anatomical feature of the patient's spine;

process the tool tracking data, the spine tracking data, and the target displacement of the at least one anatomical feature of the patient's spine to generate intraoperative navigated guidance data; and control movement of the at least one motor based on the intraoperative navigated guidance data to guide movement of the tool.

15. A method by a surgical planning system to provide computer assisted navigation for spinal surgery, the method comprising:

obtaining images of at least two different postures of a patient's spine;

measuring displacement of anatomical features of the patient's spine between the images of the at least two different postures of the patient's spine;

estimating stiffness of the patient's spine based on the measurements of displacement;

generating a patient-specific kinematic model of the patient's spine based on the estimated stiffness; and providing a surgical plan based on the patient-specific kinematic model of the patient's spine.

16. The method of claim 15, wherein estimating stiffness of the patient's spine based on the measurements of displacement, comprises:

determining flexibility of intervertebral joints of the patient's spine based on the measurements of displacement of the intervertebral joints of the patient's spine between the images of the at least two different postures of the patient's spine;

obtaining baseline biomechanical stiffness parameters of corresponding intervertebral joints of a baseline spine defined by a baseline spine model; and estimating the stiffness of the intervertebral joints of the patient's spine based on correlating the determined flexibility of the intervertebral joints of the patient's spine to the baseline biomechanical stiffness parameters of the corresponding intervertebral joints of the baseline spine defined by the baseline spine model.

17. The method of claim 16, wherein generating the patient-specific kinematic model of the patient's spine based on the estimated stiffness, comprises:

generating a 3D model of the patient's spine based on registering the anatomical features of the patient's spine imaged in at least one of the images to corresponding anatomical features of the baseline spine defined by the baseline spine model; and generating the patient-specific kinematic model of the patient's spine using the estimate of the stiffness of the intervertebral joints of the patient's spine to operationally define relationships between levels of force applied to anatomical features of the 3D model of the patient's spine to resulting displacement of the anatomical features.

18. The method of claim 17, wherein generating the computer assisted navigation data based on the patient-specific kinematic model of the patient's spine, comprises:

obtaining a target displacement of at least one anatomical feature of the patient's spine;

estimating using the patient-specific kinematic model a level of force to be applied to at least one location on the patient's spine to obtain the target displacement of the at least one anatomical feature of the patient's spine.

19. The method of claim 17, wherein generating the computer assisted navigation data based on the patient-specific kinematic model of the patient's spine, comprises:

obtaining a target displacement of anatomical features of the patient's spine through fixation of an implant to the patient's spine; and estimating using the patient-specific kinematic model a level of force that will be exerted on a surgical implant when used to fixate anatomical features of the patient's spine at the target displacement defined by the surgical plan.

20. A computer program product comprising:

a non-transitory computer readable medium storing instructions executable by a computer platform of a surgical planning system to provide computer assisted navigation for spinal surgery, the computer platform when executing the instructions is operative to:

obtain images of at least two different postures of a patient's spine;

measure displacement of anatomical features of the patient's spine between the images of the at least two different postures of the patient's spine;

estimate stiffness of the patient's spine based on the measurements of displacement;

generate a patient-specific kinematic model of the patient's spine based on the estimated stiffness; and provide a surgical plan based on the patient-specific kinematic model of the patient's spine.

* * * * *